US011915803B2

(12) United States Patent
Naeymi-Rad et al.

(10) Patent No.: US 11,915,803 B2
(45) Date of Patent: Feb. 27, 2024

(54) METHOD AND SYSTEM FOR EXTRACTING DATA FROM A PLURALITY OF ELECTRONIC DATA STORES OF PATIENT DATA TO PROVIDE PROVIDER AND PATIENT DATA SIMILARITY SCORING

(71) Applicant: Intelligent Medical Objects, Inc., Rosemont, IL (US)

(72) Inventors: Frank Naeymi-Rad, Libertyville, IL (US); Matthew Cardwell, Oak Park, IL (US); Michael DeCaro, Mount Prospect, IL (US); Erina Paul, DeKalb, IL (US); Yiqing Wang, DeKalb, IL (US); James Thompson, St. Charles, IL (US); Andrew Kanter, Highland Park, IL (US)

(73) Assignee: Intelligent Medical Objects, Inc., Rosemont, IL (US)

( * ) Notice: Subject to any disclaimer, the term of this patent is extended or adjusted under 35 U.S.C. 154(b) by 92 days.

(21) Appl. No.: 15/337,923

(22) Filed: Oct. 28, 2016

(65) Prior Publication Data

US 2018/0121604 A1 May 3, 2018

(51) Int. Cl.
*G16H 10/60* (2018.01)
*G06F 16/2457* (2019.01)
(Continued)

(52) U.S. Cl.
CPC ....... *G16H 10/60* (2018.01); *G06F 16/24578* (2019.01); *G06F 16/285* (2019.01); *G06F 40/205* (2020.01); *G16H 50/70* (2018.01)

(58) Field of Classification Search
CPC ............... G06F 16/285; G06F 16/2705; G06F 16/24578; G16H 10/60; G16H 50/70
See application file for complete search history.

(56) References Cited

U.S. PATENT DOCUMENTS 5,508,912 A * 4/1996 Schneiderman ...... G06F 19/325
                                                                  705/3
5,799,268 A    8/1998 Boguraev
(Continued)

FOREIGN PATENT DOCUMENTS

WO    WO-2016029272 A1 *  3/2016  ............. G16H 40/20

OTHER PUBLICATIONS

Genevieve B. Melton et al., "Inter-patient distance metrics using SNOMED CT defining relationships", 2006, pp. 697-705 (Year: 2006).*

(Continued)

*Primary Examiner* — Rajesh Khattar
*Assistant Examiner* — Steven G. S. Sanghera
(74) *Attorney, Agent, or Firm* — Quarles & Brady LLP

(57) ABSTRACT

A system and method for extracting data from an electronic health record to provide provider and patient data similarity scoring includes: encoding a problem list for a plurality of patients with concepts from a common electronic health record ontology. In one aspect, the patients have electronic health records maintained by a plurality of providers. The system and method then may parse the concepts into a plurality of clusters or categories and determining, for each of the providers, a total number of patients that have at least one problem in a cluster or category or determining, for each patient, which of the plurality of clusters or categories correspond to at least one concept encoded in the patient's problem list. The system and method then may calculate for each pair of providers or patients, a distance between the providers or patients.

11 Claims, 17 Drawing Sheets

Provider no. 10

| > rank_top | top_prov | Distance | rank |
|---|---|---|---|
| [1,] | 10 | 0.0000000 | 1.0 |
| [2,] | 14 | 1.0900787 | 18.0 |
| [3,] | 16 | 0.8461970 | 8.5 |
| [4,] | 22 | 0.9686442 | 16.5 |
| [5,] | 24 | 1.1276546 | 20.5 |
| [6,] | 25 | 1.1276546 | 20.5 |
| [7,] | 26 | 0.9686442 | 16.5 |
| [8,] | 41 | 0.8461970 | 8.5 |
| [9,] | 47 | 0.3918538 | 3.0 |
| [10,] | 53 | 0.9094836 | 13.5 |
| [11,] | 59 | 0.8461970 | 8.5 |
| [12,] | 64 | 0.8461970 | 8.5 |
| [13,] | 69 | 0.8461970 | 8.5 |
| [14,] | 71 | 0.4070653 | 4.0 |
| [15,] | 72 | 1.1276546 | 20.5 |
| [16,] | 73 | 0.8461970 | 8.5 |
| [17,] | 83 | 0.8148411 | 3.5 |
| [18,] | 87 | 0.9094836 | 13.5 |
| [19,] | 97 | 0.9094836 | 13.5 |
| [20,] | 100 | 0.9094836 | 13.5 |
| [21,] | 109 | 0.3422872 | 2.0 |
| [22,] | 112 | 1.1276546 | 20.5 |

(51) Int. Cl.
  *G06F 16/28* (2019.01)
  *G06F 40/205* (2020.01)
  *G16H 50/70* (2018.01)

(56) References Cited

U.S. PATENT DOCUMENTS

| | | | |
|---|---|---|---|
| 5,930,788 | A | 7/1999 | Wical |
| 6,055,540 | A | 4/2000 | Snow et al. |
| 6,101,515 | A | 8/2000 | Wical et al. |
| 6,904,432 | B2 | 6/2005 | Charlot et al. |
| 6,915,254 | B1 * | 7/2005 | Heinze .................. G06Q 50/24 704/9 |
| 7,167,858 | B2 | 1/2007 | Naeymi-Rad et al. |
| 7,496,593 | B2 | 2/2009 | Gardner et al. |
| 7,536,387 | B2 | 5/2009 | Charlot et al. |
| 7,693,917 | B2 | 4/2010 | Charlot et al. |
| 7,711,671 | B2 | 5/2010 | Meyers |
| 7,870,117 | B1 | 1/2011 | Rennison |
| 8,346,804 | B2 | 1/2013 | Phillips |
| 8,935,249 | B2 * | 1/2015 | Traub .................. G06F 16/3331 707/737 |
| 10,354,755 | B2 * | 7/2019 | Norris .................. G06Q 50/22 |
| 2002/0128861 | A1 | 9/2002 | Lau et al. |
| 2003/0179228 | A1 | 9/2003 | Schreiber et al. |
| 2005/0240572 | A1 | 10/2005 | Sung et al. |
| 2006/0069677 | A1 | 3/2006 | Tanigawa et al. |
| 2007/0179776 | A1 | 8/2007 | Segond et al. |
| 2008/0065452 | A1 | 3/2008 | Naeymi-Rad et al. |
| 2008/0201280 | A1 * | 8/2008 | Martin .................. G16H 50/20 706/12 |
| 2008/0306926 | A1 | 12/2008 | Friedlander et al. |
| 2009/0083231 | A1 | 3/2009 | Eberholst et al. |
| 2009/0150289 | A1 | 6/2009 | Joe et al. |
| 2009/0198511 | A1 * | 8/2009 | Boehlke .................. G16H 10/60 705/2 |
| 2009/0254572 | A1 | 10/2009 | Redlich et al. |
| 2010/0098306 | A1 * | 4/2010 | Madabhushi ......... G06T 7/0012 382/128 |
| 2010/0169299 | A1 | 7/2010 | Pollara |
| 2010/0262659 | A1 | 10/2010 | Christiansen et al. |
| 2011/0066425 | A1 | 3/2011 | Hudgins et al. |
| 2011/0077958 | A1 * | 3/2011 | Breitenstein ........... G06Q 10/10 705/2 |
| 2011/0138050 | A1 | 6/2011 | Dawson et al. |
| 2011/0184960 | A1 | 7/2011 | Delpha et al. |
| 2011/0288877 | A1 | 11/2011 | Ofek et al. |
| 2012/0011124 | A1 | 1/2012 | Bellegarda |
| 2012/0109683 | A1 * | 5/2012 | Ebadollahi ............. G16H 10/60 705/3 |
| 2012/0179696 | A1 | 7/2012 | Charlot et al. |
| 2012/0239671 | A1 | 9/2012 | Chaudhri et al. |
| 2013/0226616 | A1 | 8/2013 | Nigam |
| 2013/0262142 | A1 | 10/2013 | Sethumadhavan et al. |
| 2013/0268532 | A1 | 10/2013 | Doshi |
| 2013/0282713 | A1 | 10/2013 | Lawrence |
| 2015/0073943 | A1 * | 3/2015 | Norris .............. G06Q 10/06393 705/26.63 |
| 2015/0242571 | A1 * | 8/2015 | Naeymi-Rad .......... G16H 10/60 705/3 |
| 2015/0356270 | A1 | 12/2015 | Devarakonda et al. |
| 2016/0019361 | A1 | 1/2016 | Zasowski et al. |
| 2016/0063211 | A1 * | 3/2016 | Chen ...................... G16H 50/50 705/3 |
| 2017/0351819 | A1 * | 12/2017 | Yamamoto ............ G06F 16/285 |

OTHER PUBLICATIONS

International Search Report and Written Opinion, International Application No. PCT/US2017/59025, dated Jan. 25, 2018, 9 pages.
Non-Final Office Action issued in corresponding U.S. Appl. No. 14/530,727 dated Jun. 21, 2017, 16 pages.
Final Office Action issued in corresponding U.S. Appl. No. 14/530,727 dated Feb. 9, 2018, 21 pages.
Non-Final Office Action issued in corresponding U.S. Appl. No. 14/530,727 dated Jul. 2, 2018, 34 pages.
Final Office Action issued in corresponding U.S. Appl. No. 14/530,727 dated Apr. 30, 2019, 31 pages.
Bronnert et al., "Problem-Centered Care Delivery," Journal of AHIMA 83, No. 7 (Jul. 2012): 30-35.
Duch et al., "Semantic Web: Asking the Right Questions," Seventh International Conference on Information and Management Sciences, Urumchi, China, Aug. 12-19, 2008 entire document www.fizyka.umk.pl/ftp/pub/papers/kmk/08- SemWeb.pdf.
"Social tagging overview (SharePoint Server 2010)" May 12, 2010 entire document http://technet.microsoft.com/en-us/ library/ff608137.aspx.
Virginia Tech "SNOMED Core Structures 2nd AAHA Software Vendors Summit—Apr. 21, 2009".
Lee, W.-N. et al. "Comparison of ontology-based semantic-similarity measures." AMIA annual symposium proceedings. vol. 2008. American Medical Informatics Association, 2008. p. 384-388.
Melton, G. B., et al. "Inter-patient distance metrics using SNOMED CT defining relationships." Journal of biomedical informatics 39.6 (2006): 697-705.
European Patent Office. Extended European Search Report for application 17866010.6, dated Oct. 9, 2020. 14 pages.

* cited by examiner

> rank_top

|  | top_prov | Distance | rank |
|---|---|---|---|
| [1,] | 10 | 0.0000000 | 1.0 |
| [2,] | 14 | 1.0907787 | 18.0 |
| [3,] | 16 | 0.8461970 | 8.5 |
| [4,] | 22 | 0.9686442 | 16.5 |
| [5,] | 24 | 1.1276546 | 20.5 |
| [6,] | 25 | 1.1276546 | 20.5 |
| [7,] | 26 | 0.9686442 | 16.5 |
| [8,] | 41 | 0.8461970 | 8.5 |
| [9,] | 47 | 0.3918538 | 3.0 |
| [10,] | 53 | 0.9094836 | 13.5 |
| [11,] | 59 | 0.8461970 | 8.5 |
| [12,] | 64 | 0.8461970 | 8.5 |
| [13,] | 69 | 0.8461970 | 8.5 |
| [14,] | 71 | 0.4070653 | 4.0 |
| [15,] | 72 | 1.1276546 | 20.5 |
| [16,] | 73 | 0.8461970 | 8.5 |
| [17,] | 83 | 0.8148411 | 3.5 |
| [18,] | 87 | 0.9094836 | 13.5 |
| [19,] | 97 | 0.9094836 | 13.5 |
| [20,] | 100 | 0.9094836 | 13.5 |
| [21,] | 109 | 0.3422872 | 2.0 |
| [22,] | 112 | 1.1276546 | 20.5 |

Provider no. 10

Using proportion for category_top graph for patient_1 using cluster

| [1]  | 0.000000 | 3.000000 | 3.000000 | 4.358899 | 4.123106 | 3.316625 |
| [7]  | 3.316625 | 4.690416 | 3.316525 | 4.000000 | 3.464102 | 5.000000 |
| [13] | 3.000000 | 2.645751 | 2.828427 | 3.162278 | 4.000000 | 4.472136 |
| [19] | 5.099020 | 6.928203 | 3.316625 | 3.000000 | 3.000000 | 3.000000 |
| [25] | 3.316625 |          |          |          |          |          | graph for patient_1 using category

| [1]  | 0.000000 | 3.316625 | 3.316625 | 4.795832 | 4.358899 | 3.872983 |
| [7]  | 3.872983 | 6.782330 | 3.872983 | 4.472136 | 3.464102 | 5.744563 |
| [13] | 3.605551 | 2.645751 | 2.828427 | 3.464102 | 3.741657 | 4.898979 |
| [19] | 5.477226 | 7.348469 | 3.872983 | 3.316625 | 3.316625 | 3.316625 |
| [25] | 3.872983 |          |          |          |          |          | graph of lexical for patient_1

| [1]  | 0.000000 | 2.828427 | 2.828427 | 2.828427 | 2.449490 | 2.828427 |
| [7]  | 2.828427 | 2.828427 | 2.828427 | 2.828427 | 2.828427 | 2.645751 |
| [13] | 2.828427 | 2.645751 | 2.449490 | 2.828427 | 2.645751 | 2.828427 |
| [19] | 2.828427 | 2.645751 | 2.828427 | 2.828427 | 2.645751 | 2.828427 |
| [25] | 2.828427 |          |          |          |          |          | graph of 0.5*lexical+0.5*cluster for patient_1

| [1]  | 0.000000 | 5.828427 | 5.828427 | 7.187326 | 6.572595 | 6.145052 |
| [7]  | 6.145052 | 7.518843 | 6.145052 | 6.828427 | 6.292529 | 7.645751 |
| [13] | 5.828427 | 5.291503 | 5.277917 | 5.990705 | 6.645751 | 7.300563 |
| [19] | 7.927447 | 9.573955 | 6.145052 | 5.828427 | 5.645751 | 5.828427 |
| [25] | 6.145052 |          |          |          |          |          | graph of 0.2*lexical+0.8*cluster for patient_1

| [1]  | 0.000000 | 2.965685 | 2.965685 | 4.052805 | 3.788382 | 3.218985 |
| [7]  | 3.218958 | 4.318018 | 3.218985 | 3.765685 | 3.336967 | 4.529150 |
| [13] | 2.965685 | 2.645751 | 2.752640 | 3.095508 | 3.729150 | 4.143394 |
| [19] | 4.644901 | 6.071713 | 3.218985 | 2.965685 | 2.929150 | 2.965685 |
| [25] | 3.218985 |          |          |          |          |          |

METHOD AND SYSTEM FOR EXTRACTING DATA FROM A PLURALITY OF ELECTRONIC DATA STORES OF PATIENT DATA TO PROVIDE PROVIDER AND PATIENT DATA SIMILARITY SCORING

BACKGROUND

1. Field of the Invention

The present application is directed to electronic health record or other electronic patient data repository tools, including analytical tools for effectively using data encoded within electronic health records or other data repositories.

2. Description of the Related Art

Electronic medical ontologies, also known as medical classification codes, are necessary with the implementation and proliferation of electronic medical records. Various ontologies have been developed for various reasons, including administrative code sets that may be designed to support administrative functions of healthcare, such as reimbursement and other secondary data aggregation; clinical code sets that encode specific clinical entities involved in clinical work flow and allow for meaningful electronic exchange and aggregation of clinical data for better patient care; and reference terminology code sets that may be considered a "concept-based, controlled medical terminology" to maintain a common reference point in the healthcare industry. Reference terminologies also identify relationships between their concepts, e.g., relationships can be hierarchically defined, such as a parent/child relationship. Common examples of administrative code sets are the International Classification of Disease (ICD) and the Current Procedural Terminology, which is referred to via the trademark CPT. Examples of clinical code sets are the Logical Observation Identifiers Names and Codes, referred to under the trademark LOINC, and a normalized terminology for medication information, such as the terminology of the National Library of Medicine referred to under the trademark RxNorm. One example of a reference terminology is The Systematized Nomenclature of Medicine—Clinical Terms, referred to under the trademark "SNOMED CT."

One challenge with implementing an electronic medical ontology is to ensure the accuracy and completeness of recordkeeping, at the time of the patient visit or otherwise during data entry. One method of structuring and codifying the data to achieve this goal includes implementing an interface terminology that recognizes semantic meaning, mapping that interface terminology to the various other ontologies, and then relying on that interface terminology to analyze the practitioner's entries. One example of a system and method for using an interface terminology and the relevant ontology mappings may be found in the commonly-owned U.S. patent publication 2014/0122117, published May 1, 2014, the contents of which are incorporated by reference in their entirety. In that example, the interface terminology comprises a plurality of concepts within one or more domains, and one or more descriptions (lexicals) linked to each concept, where each description reflects an alternative way to express the concept.

Separately, care providers across all disciplines see myriad patients presenting with various problems. Often, treatment of those patients is fairly straightforward, as the problems are those with which the care providers deal frequently or for which treatment plans are commonly known. At times, however, the provider may face a problem or combination of problems with an unknown or more rare treatment protocol, and it may be desirable to draw upon the knowledge and experience of other providers in addressing those problems. While the ontologies described above may be useful for recordkeeping, billing, etc., the sheer volume of codes or entries within each ontology may hinder searching and meaningful analysis. For example, within ICD-10-CM, there are almost 70,000 distinct diagnosis codes to which particular problems can be mapped, and there are an additional 87,000 distinct codes within ICD-10-PCS for mapping procedure-related data. Additionally, due to various other constraints, including geography, patient confidentiality, etc., finding the relevant information may be difficult and time consuming, if not seemingly impossible.

Still further, instead of looking outward, care providers may be able to draw upon their own internal knowledge and previous experience in addressing a problem or combination of problems. In this regard, the volume of patients seen by the provider or the amount of time elapsed between the current instance of a problem or combination of problems and the relevant previous instance may hamper the provider's recall of the relevant details.

What are needed are a system and method that preferably address one or more of these challenges.

BRIEF SUMMARY

In one aspect, a method for extracting data from an electronic health record to provide provider and patient data similarity scoring includes: encoding a problem list for a plurality of patients with concepts from a common electronic health record ontology, wherein the plurality of patients have electronic health records maintained by a plurality of providers, parsing the concepts into a plurality of clusters or categories, determining, for each of the providers, a total number of patients that have at least one problem in a cluster or category, iterating the determining step for each of the remaining clusters or categories, and calculating, for each pair of providers, a distance between the providers.

In another aspect, a method for extracting data from an electronic health record to provide provider and patient data similarity scoring includes: encoding a problem list for a plurality of patients with concepts from a common electronic health record ontology, parsing the concepts into a plurality of clusters or categories, determining, for each patient, which of the plurality of clusters or categories correspond to at least one concept encoded in the patient's problem list, and calculating, for each pair of patients, a distance between the patients.

DETAILED DESCRIPTION

Figure 1:
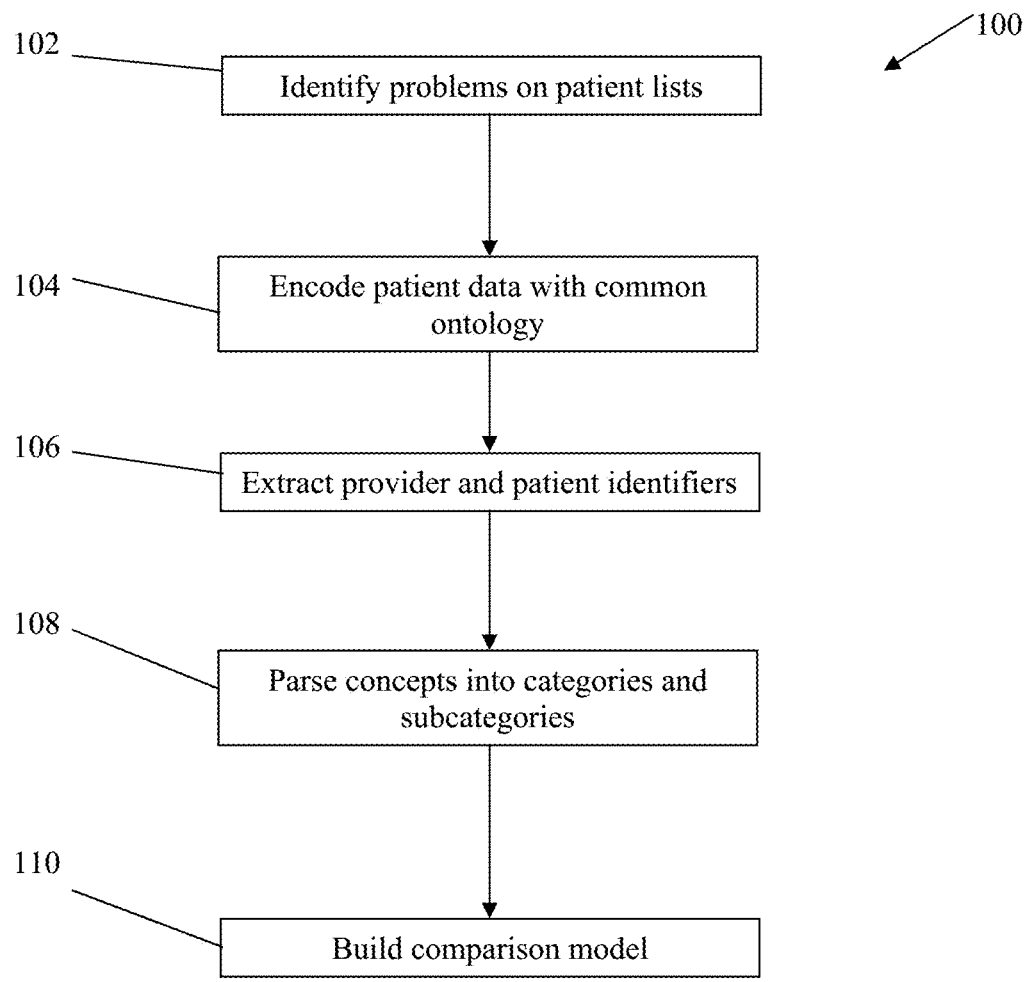
FIG. 1 is a flowchart depicting one example of a method for extracting data from a patient problem list, e.g., a problem list stored in or accessible by an electronic health record, to provide provider and patient data similarity scoring.

As set forth in greater detail herein, the present system and method are operable within a network of computer systems, with a plurality of computers each having a processor configured to operate electronic health record ("EHR") software accessible by one or more care providers to document patient encounters. In one aspect, each computer system operates the same EHR software. In another aspect, the computer systems may operate different EHR software packages that receive and/or store patient data in different ways. In this latter aspect, however, the various EHR software packages may interface with a common ontology such as an interface terminology in order to provide a common encoding mechanism for their respective sets of patient data.

The computer systems may be interconnected as part of a common network servicing a single entity, such as a solo practitioner or a physician's office. Alternatively, the computer systems may be separately configured to serve a plurality of related entities, such as a hospital or a group of affiliated providers. In yet another option, the computer systems may be configured to serve a plurality of unrelated entities, such as unaffiliated care providers. In each instance, patient records may be stored in a database in each computer system or in a centralized database operatively coupled to each respective computer. Additionally, in any of these instances, the computer systems may be in communication with a centralized computer system, which may include one or more servers configured to distribute the common ontology to each of the computer systems. The centralized computer system also may receive patient-related data from each of the other computer systems.

Each EHR software package may include, as one component, a patient problem list that maintains a history of all patient problems. The problem list may distinguish between current and past problems, as well as chronic versus acute problems, in order to give providers an accurate picture of each patient's history. Each entry in the problem list may be encoded with an entry from one or more different ontologies, permitting the EHR to interact with other software applications. For example, each problem may be encoded with a SNOMED code or an ICD code to facilitate recordkeeping and diagnosis, and orders or other procedures associated with each problem also may be encoded with a CPT code to facilitate billing and reimbursement.

In addition to problem lists, the EHR also may maintain a list of test results for each patient, as well as a history of all procedures recommended to and/or performed on each patient. In the former case, each test result record may be encoded with an ontological code such as a LOINC code. In the latter case, each procedure may be encoded with an ontological code, again, such as a CPT code.

In each of the instances set forth above, the data in the EHR may be encoded with one or more interface terminology concepts—directly or indirectly. In the case of indirect encoding, the EHR entry may be encoded with an interface terminology description. Rather than being related hierarchically to concepts, each description instead may be an alternative way to express a concept. Each interface terminology concept may be mapped to one or more of the various administrative, clinical, or reference codes, permitting the EHR to retain all of the necessary mapping without devoting memory, storage, or other system resources to maintaining those maps for every single patient record.

Additionally or alternatively, each computer may be configured to execute patient problem list software and/or access patient problem list data independent of executing EHR software. Such data may reside, for example in a data repository such as a data warehouse (including the problem list software's log repository) or a health information exchange. In this latter alternative, the patient problem list data may originate from one or more sources, including being generated by EHR software, being aggregated from scanned documents via a transcription service, or being received as free-text data input.

One example of a system and method for maintaining a problem list by mapping to elements of an interface terminology is disclosed in the commonly-owned U.S. patent publication 2015/0242571, published Aug. 27, 2015, the contents of which are incorporated by reference in their entirety.

Whether the data for the present method originates from patient-centric EHR data or from independent or separate problem list data, that data may include the practitioners' requests and generated response data, e.g., a problem list entry, a procedure entry, etc. That data also may be tagged with enough information to be able to distinguish patients and providers from one another, e.g., each provider may be assigned a unique identifier and each patient may be provided with a separate unique identifier, either on a per-provider or an overall basis. The data will also include a set of problems and the interface terminology problems to which those problems have been associated. Additionally, the data may include demographic information such as age, gender, and location. Still further, the data may include ancillary information such as medications, lab results, etc., in order to provide for more robust analysis among patients. Moreover, additional data such as malformed requests, test requests and improperly entered identifiers (organization, provider, and/or patient) may remain in the data repository but may be ignored.

Once patient data generally, and patient problem list data in one aspect, specifically, have been encoded with an ontology common to multiple provider systems, it may be possible to identify all problems on a single patient's problem list. Using that same information, the system then may be configured to identify providers who have similar case mixes among their patient sets, while also maintaining confidentiality and privacy of each provider's patient data. As explained in greater detail below, given the input of a plurality of patient problem lists, the system may return a list or graphical display of resulting entity matches, ranked by similarity.

Additionally, the system may be configured to provide results in multiple use cases. In a first instance, the system may be provider-centric, such that a provider may seek one or more other providers that are similarly matched to the provider's practice, i.e., one or more providers caring for a similar population. This application may be particularly useful to a practitioner diagnosing and/or treating a patient with less commonly-seen symptoms, such that the practitioner may be able to consult with or draw on the experience of one or more relevant providers.

This application also may be useful to a provider in order to analyze the practitioner's case mix as compared to that of other providers, in order to evaluate one or more patient statistics and to see how those statistics match up against those from the other providers. In one aspect, a plurality of problem list entries may be used to generate a Hierarchical Condition Category (HCC) or a Diagnosis-Related Group (DRG) code for the patient, and the identity of those codes may vary based on a multiplicity of factors including, e.g., the problems identified as part of the group, the identity of a "primary" versus one or more "secondary" problems, the existence of complications, the presence of co-morbidities, etc. Practitioners, thus, may use the present system to evaluate or compare patients with complex problem lists to determine whether those patients are being documented similarly. Similarly, practitioners may use the present system to determine whether they are making similar referrals to similarly-situated patients.

In a second instance, the system may be patient-centric, in which a provider may seek out one or more patients within that provider's patient list that have the same or similar problem list as a reference patient. The same HCC and DRG functionality discussed above also may apply in this instance, with the practitioner being able to analyze his or her own patient set for similarities.

Briefly, and with reference to FIG. 1, the method 100 may include the step of identifying 102 problems on one or more providers' one or more patient lists. In one aspect, the identifying step may include encoding 104 the patient data with a common ontology. From there, the method may extract 106 user or provider identifiers and identifiers for each of the one or more patients. The method then may include the step of parsing 108 the ontology concepts into categories and subcategories. Once those concepts are parsed, the method may include building 110 a comparison model by finding similarly-situated providers or patients, and multiple examples for deriving those similarities are discussed in greater detail below.

Categorization and Clustering of Problem List Elements

Figure 2:
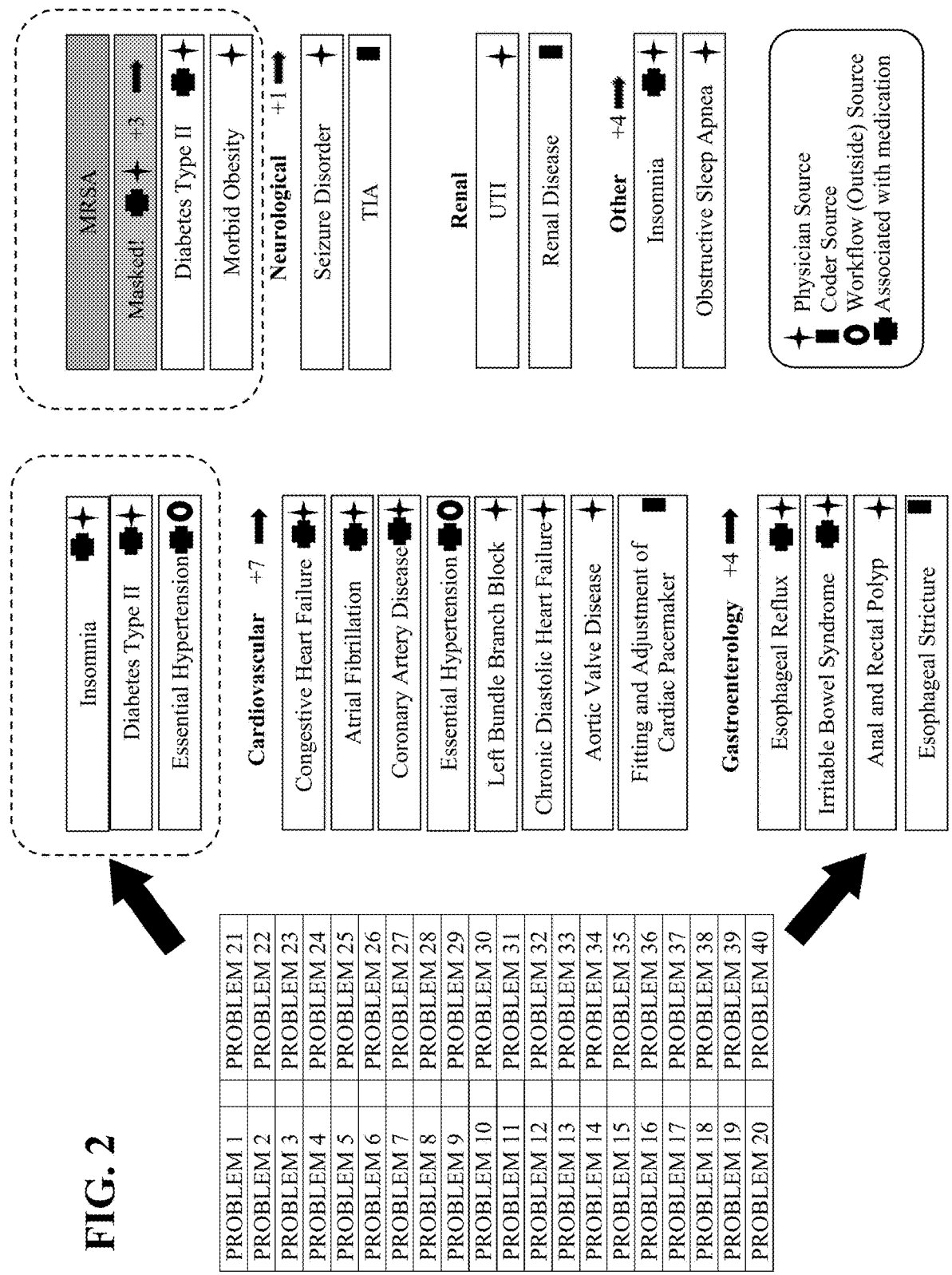
FIG. 2 is a depiction of a method of reconciling a general problem list into one or more clinical categories based on concept groupings. In this case the concept group is related to clinical specialties such as Gastroenterology or Cardiovascular. Many different concept groupings can be enabled using the methods described.

As seen in FIG. 2, a method for processing electronic medical record problem lists may be employed to generate a clinically relevant patient profile. In one aspect, the patient profile may be useful to a clinician because it may categorize and group related problems according to concept groupings, and groupings may be determined based on semantic distance between the represented concepts. For example, all cardiovascular problems may be grouped under a "cardiovascular" category, all kidney-related problems may be grouped under a "renal" category, etc.

In addition, the system may attach indicator flags to the problems within each category, which may permit later ranking and ranked display of the problems according to attributes, such as severity, timeliness, or other concepts such as classification within a clinical measure. One example of such a flag is seen in FIG. 2, in which the problem "Diabetes mellitus" and the related problems clustered underneath that summary problem are marked with a CQM flag. The system may apply an indicator flag to the summary problem if any of its clustered problems (as that term is discussed in greater detail below) include the flag.

The CQM, i.e., Clinical Quality Measurement, flag indicates that its associated problem element must comply with CQM requirements for treatment and documentation in order to be eligible for the reimbursements provided for such compliance. Thus, a problem having this flag may be presented to the user as a higher value or higher priority problem element. In addition to having the flag callout, this flag also may be used as a factor in problem list ranking. For example, CQM problems may be ranked and presented higher on the problem list within each category than other, non-flagged problem elements.

Other potential flags may include HCC (Hierarchical Condition Category), CC (Complication and Comorbidity), and MCC (Major Complication and Comorbidity). One of ordinary skill in the art would appreciate that values associated with these terms are reflective of the severity of their underlying problems. As such, problems flagged with one or more of these flags may provide a visual indicator to the user that they may need to be addressed with higher priority than other problems on the list.

Returning to FIG. 2, multiple criteria in addition to the indicator flags may be applied to the problems in order to determine the rankings within these lists. For example, problems that are associated with/require medication may be ranked higher than those that are/do not. Problems that are entered by a physician/clinician may be ranked higher than those that are sourced from other entities later in the record review process, e.g., by a coder or other administrative personnel. Problems that are obtained from workflow or some other outsider source, e.g., those problems that may be extracted from review of the patient's chart may rank somewhere in between clinician- and coder-generated problems (assuming all other factors are the same). Problem entries may be time-stamped, such that more recent problems may be ranked higher than older problems.

The system also may generate lists in order to call attention to problems that may require more immediate attention or problems that may affect multiple disciplines. For example, another possible category may be an "in focus now" category, which may display those problems currently most relevant to the user, regardless of whether the problem also can fit into one of the other categories described above, and a "special display" category, which may list high priority problems of extreme, immediate importance, or of problems which are always part of the patient's overall baseline health state. These problems may be categorized more specifically, but they may have effects that cross disciplines, such that the clinician may desire to know about them when addressing the specific problems within his or her discipline.

This mapping may serve as the basis for the categorization, grouping, rolling up, nesting, etc., of the entries in a problem list. Certain interface terminology concepts may be related to other interface terminology concepts based on similar subject matter. For example, there may be a plurality of concepts that pertain to cardiac conditions. Thus, all problems that map to these concepts may be grouped together for categorization and display such as that shown in FIG. 2.

In addition to the ranking or sorting criteria describe above, these outside vocabulary mappings may be an additional factor used to rank the problem list entries. For example, mappings to some established terminologies or vocabularies may be used to perform the mapping/grouping described in the previous paragraph, and mappings to a second terminology or vocabulary or a proprietary mechanism may be used to sort more specifically within the determined categories.

Figure 3:
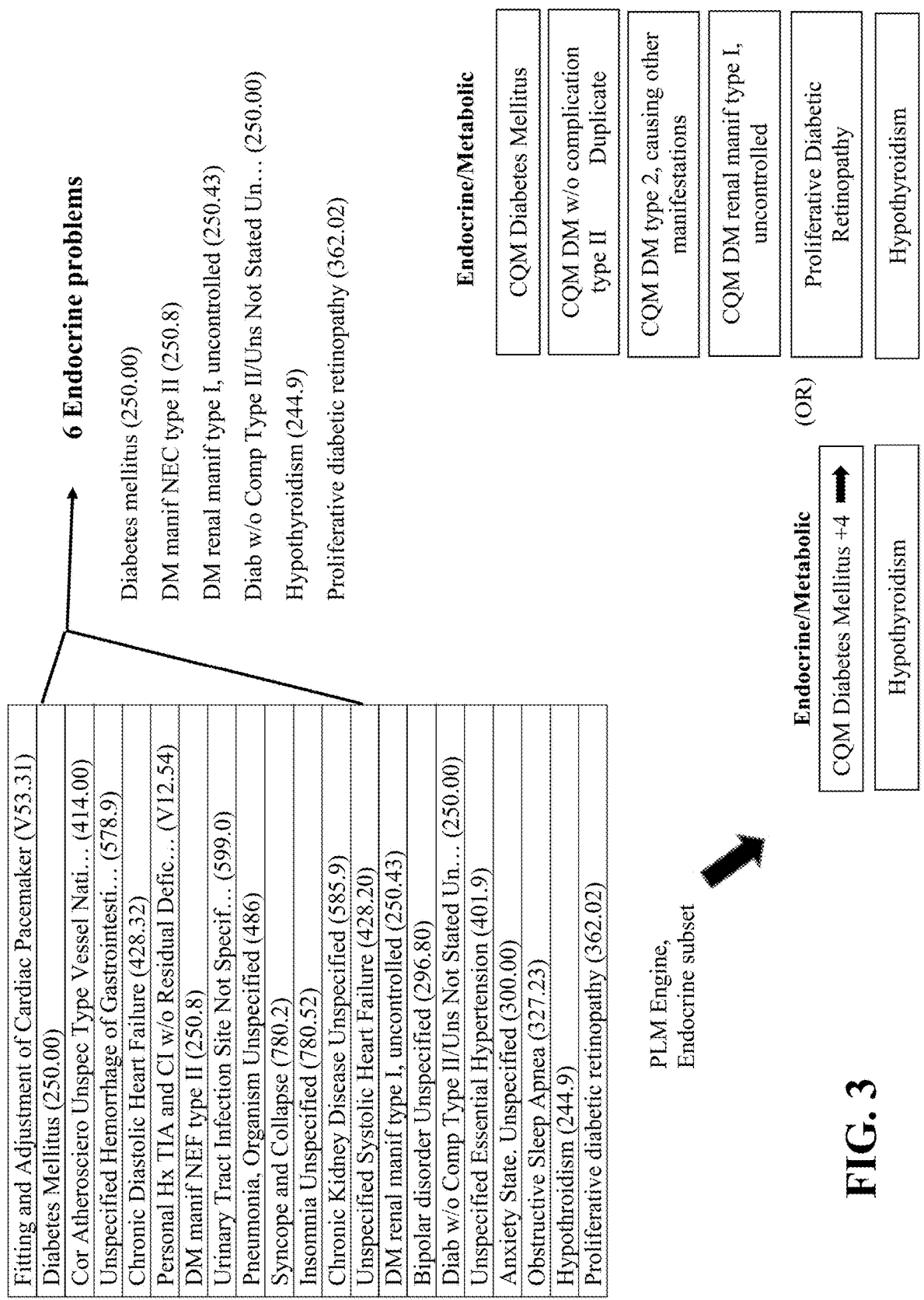
FIG. 3 is a depiction of exemplary relationships between problem list elements within a clinical category and an example of how problems can be nested together or seen in full detail.

Turning now to FIG. 3, it will be seen that certain problems not only fall within the same category as other problems but that they also may be considered subsets of another problem, i.e., they may be clusters within that problem. These relationships can be determined and managed by using the interface terminology, which also may recognize that certain concepts are more general than others and thus are hierarchically related to those other concepts. The system may group these more specific concepts underneath the more general, parent concept, thereby further arranging the problem list, whose entries may be mapped to these sub-concepts. As it relates to presentation of these problem list entries, the system may display in the problem list the problem that maps to the more general, parent concept and an indicator that other problem entries are nested or clustered and may be viewable under that parent problem, e.g., by clicking on the indicator.

In one aspect, clustered problem elements underneath a more general, parent concept may be ranked or organized using one or more of the criteria discussed above for ranking elements within the problem list generally. Alternatively, as seen in FIG. 3, clustered problem elements may be arranged using a more simplistic algorithm, e.g., they may be arranged alphabetically. In still another aspect, the system may rank flagged problems above non-ranked problems and then apply the more simplistic algorithm within each of those subsets. In any event, the system may allow user customization, permitting the user to rearrange the ordering of elements both in the problem list and within the clustered subsets, as discussed below.

From a database management perspective, clustered problems may be stored as a list of elements in a flat file database, with each element pointing to its parent problem element. Alternatively, clusters may be sub-trees in a hierarchical database structure underneath their respective category elements.

To this point, the patient list has been described as being patient specific, i.e., each patient has his or her own list, with entries specific to that patient in order to accurately record the patient's problem history. The system and method may function similarly as a way to bring a clearer clinical picture for a population aggregator, i.e., determining what problems exist for a given population, or for a given patient who may have multiple problems culled from multiple sources within a large data warehouse. In that case, the number of problems in the aggregated list may be larger (likely significantly larger) than for an individual record within an EHR, although the methodology may remain the same, i.e., each problem may be mapped to an interface terminology concept, concepts may be grouped and ordered, and the ordered problems then may be available for logical display and analysis.

Figure 4:
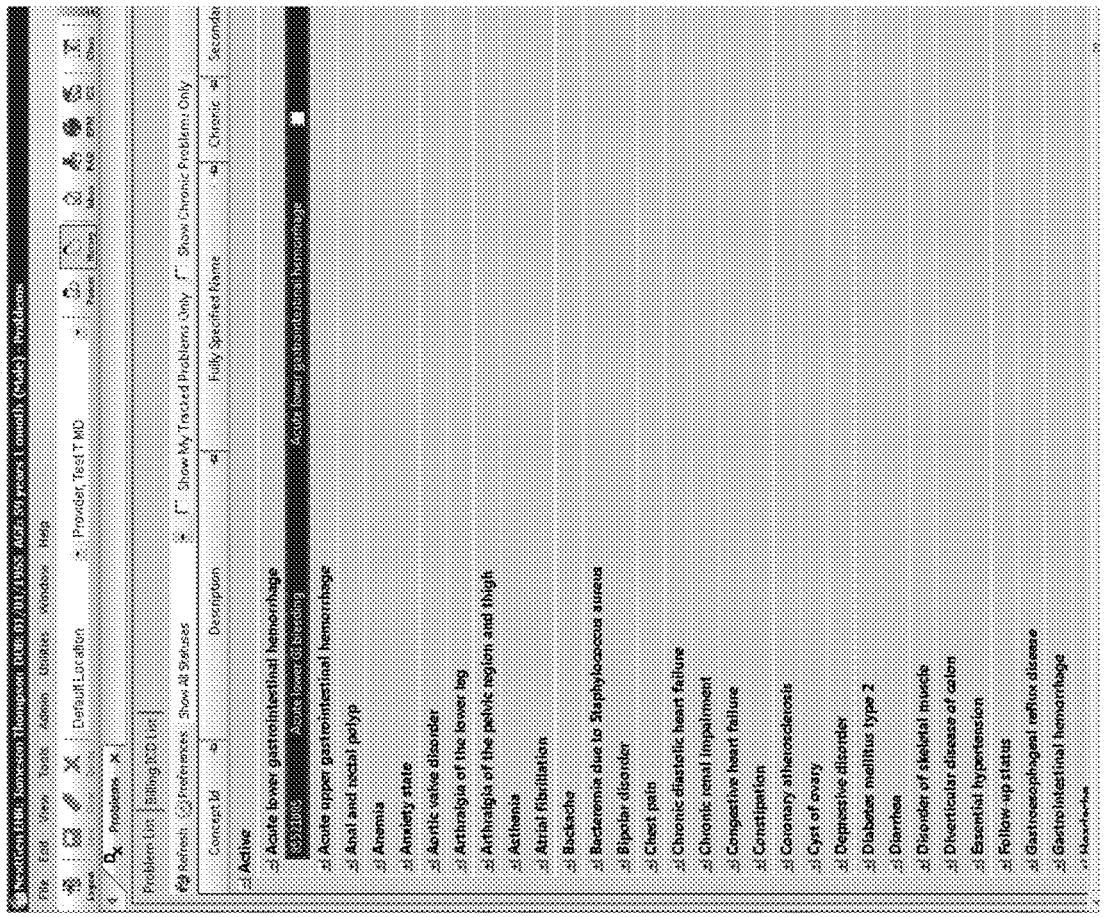
FIG. 4 is a depiction of problem lists from different sources, illustrating differences in the way in which problem list elements are arranged and displayed.

As seen in FIG. 4, and as discussed above, another issue with problem lists may become evident when attempts are made to combine lists from multiple different sources. These sources may format, store, and/or represent elements in the list differently from one another and not in a consistent format.

In order to accomplish reconciliation of elements within a single list (i.e., grouping problems within a list into categories and establishing clusters within those categories, which may or may not include the step of combining elements from multiple problem lists into a single list), the system may create an anchoring term from an interface terminology foundation technology that permits creation of a semantic distance between any two other terms from external vocabularies. This anchoring term may be considered a central concept within an interface terminology. In one aspect, determining this anchoring term may be achieved by a concept tagging method, and examples of such a method may be found in the commonly-owned U.S. Pat. No. 9,418,150, issued Aug. 16, 2016, the contents of which also are incorporated by reference herein in their entirety.

Data Structure—Providers

Figure 5:
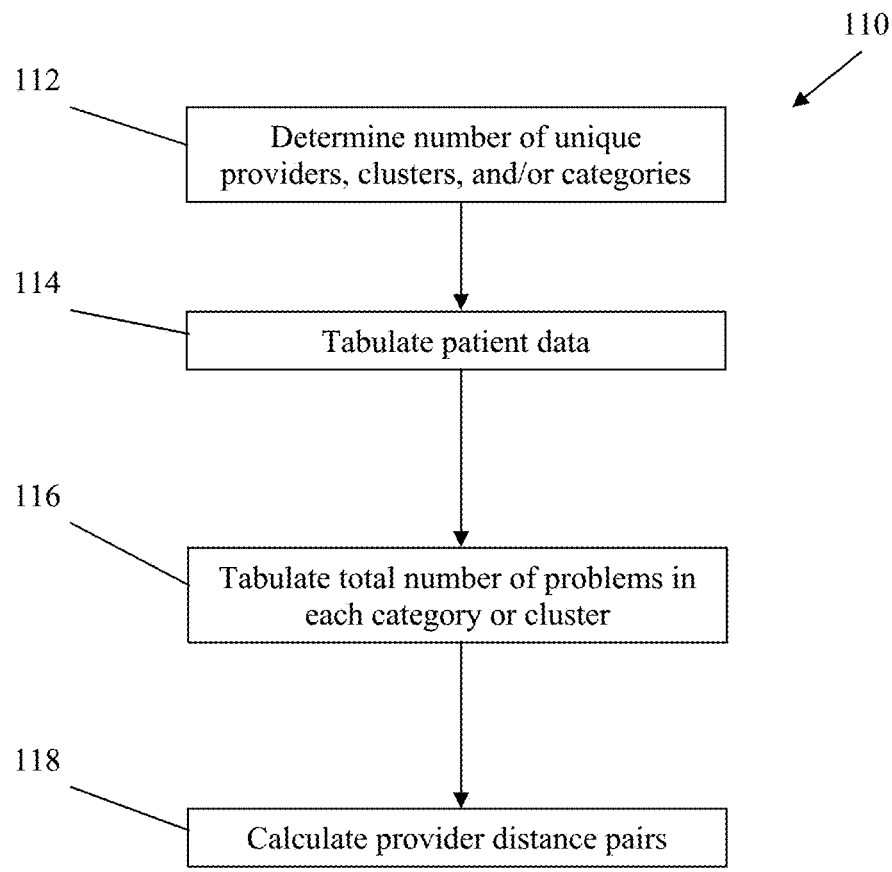
FIG. 5 is a flowchart depicting a subroutine of the method of FIG. 1 directed to a provider-centric aspect of the method.

With reference to FIG. 5, in a provider-centric case, the building step may include, for each provider, determining 112 a number of unique providers, unique clusters, and/or unique categories. The building step then may include tabulating 114 a number of distinct patients having at least one problem in a given set of categories, which may include generating a table containing patient counts, partitioned by cluster (or category) for each provider, and counting/summing the total number of patients for each provider. The building step further may include tabulating 116 a total number of problems for the provider in those categories and calculating 118 a distance in pair-wise comparison from each provider to a plurality of other providers, and, preferably, to every other provider in order to determine how far away the provider's case mix is from other providers.

For example, consider a single arbitrary provider, $Pr_x$, with 4 clusters, i.e., $cl_x$; x=1; 2; 3; 4, and 3 patients, i.e., $Pa_y$; y=1; 2; 3. The following table depicts the determining step 112, determining how many problems in each cluster a given patient may have in this example:

| Patient | Cluster | | | |
| --- | --- | --- | --- | --- |
| | $cl_1$ | $cl_2$ | $cl_3$ | $cl_4$ |
| $Pa_1$ | 20 | 32 | 0 | 15 |
| $Pa_2$ | 19 | 0 | 51 | 73 |
| $Pa_3$ | 9 | 0 | 15 | 3 |

The next table then depicts the tabulating step 114, counting how many patients have at least one problem in the given clusters. For example, each cell in the following table is the sum of the number of non-zero rows in the respective column of the previous table:

| Provider | Cluster | | | |
| --- | --- | --- | --- | --- |
| | $cl_1$ | $cl_2$ | $cl_3$ | $cl_4$ |
| $Pr_x$ | 3 | 1 | 2 | 3 |

The process may be iterated for each provider and each cluster within the data set, yielding a table of provider-cluster count entries.

Data Structure—Patients

Figure 6:
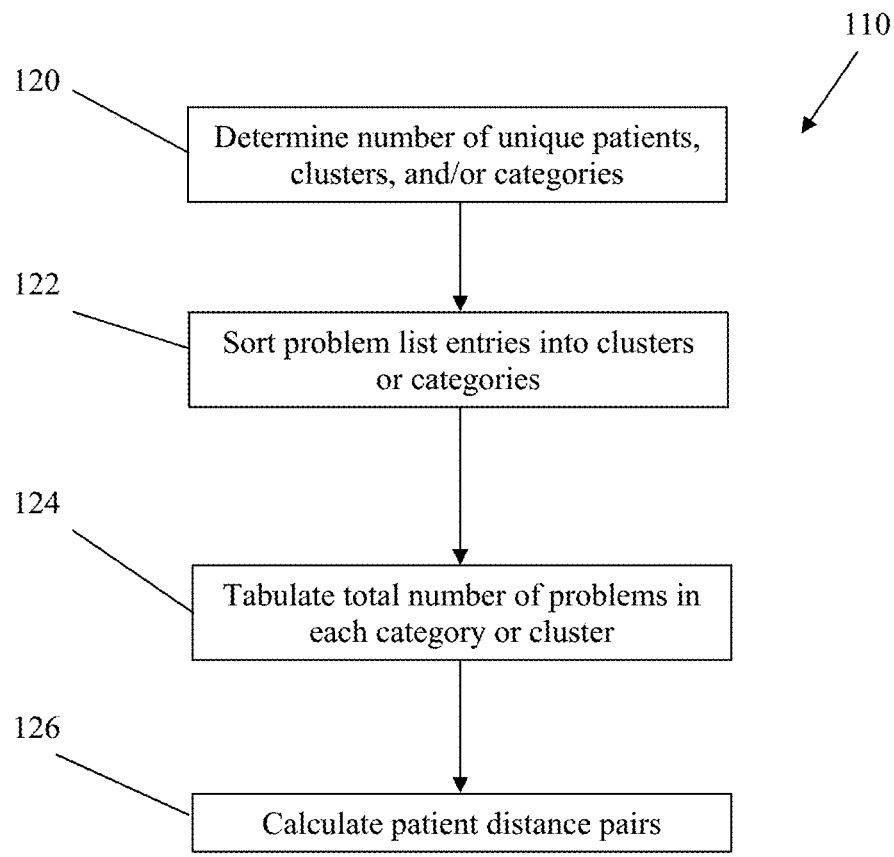
FIG. 6 is a flowchart depicting a subroutine of the method of FIG. 1 directed to a patient-centric aspect of the method.

With reference to FIG. 6, in a patient-centric case, the building step may include, for each provider, determining 120 a number of unique patients, unique clusters, and/or unique categories. The building step then may include sorting 122 each patient's problem list entries into one of the clusters or categories to generate a table containing cluster or category counts for each of the provider's patients. The building step further may include tabulating 124 a total number of problems for each patient in those categories and calculating 126 a distance in pair-wise comparison from each of the provider's patients to each of the provider's other patients in order to determine how far away the patients' problem list mixes are from the other patients.

For example, for a set of problem clusters for an arbitrary (high-activity) provider, the determining step 120 may result in 25 patients, with problems in 33 clusters and 17 categories.

For the same provider/cluster/patient combination as in the first example, if any patient went to the provider for a specific problem, the system may consider it as a "1," yielding:

| Patient | Cluster | | | |
| --- | --- | --- | --- | --- |
| | $cl_1$ | $cl_2$ | $cl_3$ | $cl_4$ |
| $Pa_1$ | 1 | 1 | 0 | 1 |
| $Pa_2$ | 1 | 0 | 1 | 1 |
| $Pa_3$ | 1 | 0 | 1 | 1 |

The system will perform further analytics on this data set in order to determine relative similarities between providers and/or patients, as discussed in greater detail below.

Data Structure—Partitioned by Time

Both the provider- and the patient-centric aspects described above may use patient data going back to when the electronic health records or problem list entries first were used to start recording encounter data. Alternatively, the system may parse the records into temporal segments, e.g., monthly segments, such that the matrices depicted above may become three-dimensional, with the third dimension (depth) being time. In that instance, the sum of the depth rows then may be the matrices depicted above.

In another instance, the system may be configured to let a user select an earliest time before which any data will be excluded, e.g., the past 5 years or 1 year. Still further, the system may be configured to receive a user input of a specific time period from which data is extracted, e.g., between the previous April 1 and June 30.

Patient Distance Calculation Methodology

Once the patient data in either aspect described above has been determined, the system may be configured to calculate a count of patients for each provider with at least one problem in each cluster or category.

Patient counts may fluctuate quite highly from provider to provider and are not bounded above, as the number may increase as the practitioner sees more patients over time. As such, it may be more consistent to normalize the data, e.g., by reporting proportions of patients with problems that present in each cluster rather than absolute counts. Using proportions means that the patient count is always bounded between 0 and 1, inclusive. Additionally, rather than discrete patient count numbers, a proportional representation utilizes a continuous scale.

Whether using absolute values or proportions, the system then may calculate distance measurements for each provider based on those values or proportions.

One technique for identifying a distance between two providers is to use a Minkowski distance of order 2 (2-norm). That distance is calculated as the square root of the sum of the differences between cluster or category proportions, i.e.:

$$d_{ik} = \sqrt{\Sigma_{i \neq k, j}(P_{ij} - P_{kj})^2}$$

where:

$d_{ik}$ is the distance between provider i and provider k;

$$P_{ij} = \frac{c_{ij}}{c_i},$$

i.e., a proportion of patients for provider i with at least one problem in a cluster or category j, $c_{ij}$ is the number of patients for provider I with at least one problem in cluster (category) j, $c_i$ is the total number of patients for provider i.

In this manner, patient problem lists that include multiple problems within a cluster are weighted more heavily than clusters for which only a single problem appears, reflecting that the former situation may signify a more detailed or complicated case mix.

The distance calculation may be iterated for each provider pairing, generating a distance matrix:

| Provider | $Pr_1$ | Pr2 | ... | Pri | ... | Prj | ... | Prn |
| --- | --- | --- | --- | --- | --- | --- | --- | --- |
| $Pr_1$ | 0 | $d_{12}$ | ... | $d_{1i}$ | ... | $d_{1j}$ | ... | $d_{1n}$ |
| $Pr_2$ | $d_{21}$ | 0 | ... | $d_{2i}$ | ... | $d_{2j}$ | ... | $d_{2n}$ |
| . | . | . | | . | | . | | . |
| . | . | . | | . | | . | | . |
| $Pr_i$ | $d_{i1}$ | $d_{i2}$ | ... | 0 | ... | $d_{ij}$ | ... | $d_{in}$ |
| . | . | . | | . | | . | | . |
| . | . | . | | . | | . | | . |
| $Pr_n$ | $d_{n1}$ | $d_{n2}$ | ... | $d_{ni}$ | ... | $d_{nj}$ | ... | 0 |

In this case, $d_{ij} = d_{ji}$, so that the matrix is symmetric.

|        | [, 1]  | [, 2]  | [, 3]  | [, 4]  | [, 5]  | [, 6]  | [, 7]  | [, 8]  | [, 9]  | [, 10] |
|--------|--------|--------|--------|--------|--------|--------|--------|--------|--------|--------|
| [1,]   | 0.0000 | 1.8048 | 0.9743 | 0.5519 | 0.8130 | 1.2877 | 0.7178 | 0.8683 | 1.6767 | 0.6844 |
| [2,]   | 1.8048 | 0.0000 | 2.1985 | 1.7023 | 1.6250 | 1.9365 | 1.9597 | 1.7957 | 2.6458 | 1.9277 |
| [3,]   | 0.9743 | 2.1985 | 0.0000 | 0.9877 | 1.2970 | 1.4434 | 1.2047 | 1.1995 | 1.1785 | 1.1837 |
| [4,]   | 0.5519 | 1.7023 | 0.9877 | 0.0000 | 0.6621 | 1.2574 | 0.9628 | 0.7858 | 1.7726 | 0.5366 |
| [5,]   | 0.8130 | 1.6250 | 1.2970 | 0.6621 | 0.0000 | 1.5052 | 1.1094 | 1.0216 | 2.0143 | 0.8138 |
| [6,]   | 1.2877 | 1.9365 | 1.4434 | 1.2574 | 1.5052 | 0.0000 | 1.4743 | 1.3534 | 1.9365 | 1.4604 |
| [7,]   | 0.7178 | 1.9597 | 1.2047 | 0.9628 | 1.1094 | 1.4743 | 0.0000 | 1.0880 | 1.6008 | 1.0278 |
| [8,]   | 0.8683 | 1.7957 | 1.1995 | 0.7858 | 1.0216 | 1.3534 | 1.0880 | 0.0000 | 1.7555 | 0.9698 |
| [9,]   | 1.6767 | 2.6458 | 1.1785 | 1.7726 | 2.0143 | 1.9365 | 1.6008 | 1.7555 | 0.0000 | 2.0123 |
| [10,]  | 0.6844 | 1.9277 | 1.1837 | 0.5366 | 0.8138 | 1.4604 | 1.0278 | 0.9698 | 2.0123 | 0.0000 |

While the distances above were calculated using a 2-norm, it may be possible to calculate those distances in other ways such as, e.g., by using a 1-norm or an infinity- (or max-)norm. In the former case, the 1-norm is a sum of the absolute value of the differences between the P values, and in the latter case, the infinity- (or max-) norm is the maximum absolute difference between the P values.

Once distances are calculated, clusters may be arranged to indicate similarity between providers. One example of this arrangement may be seen in FIG. 7. In that figure, each circle represents a provider, with the number in the circle corresponding to a provider ID. The various groups of circles reflect clusters.

Figure 7:
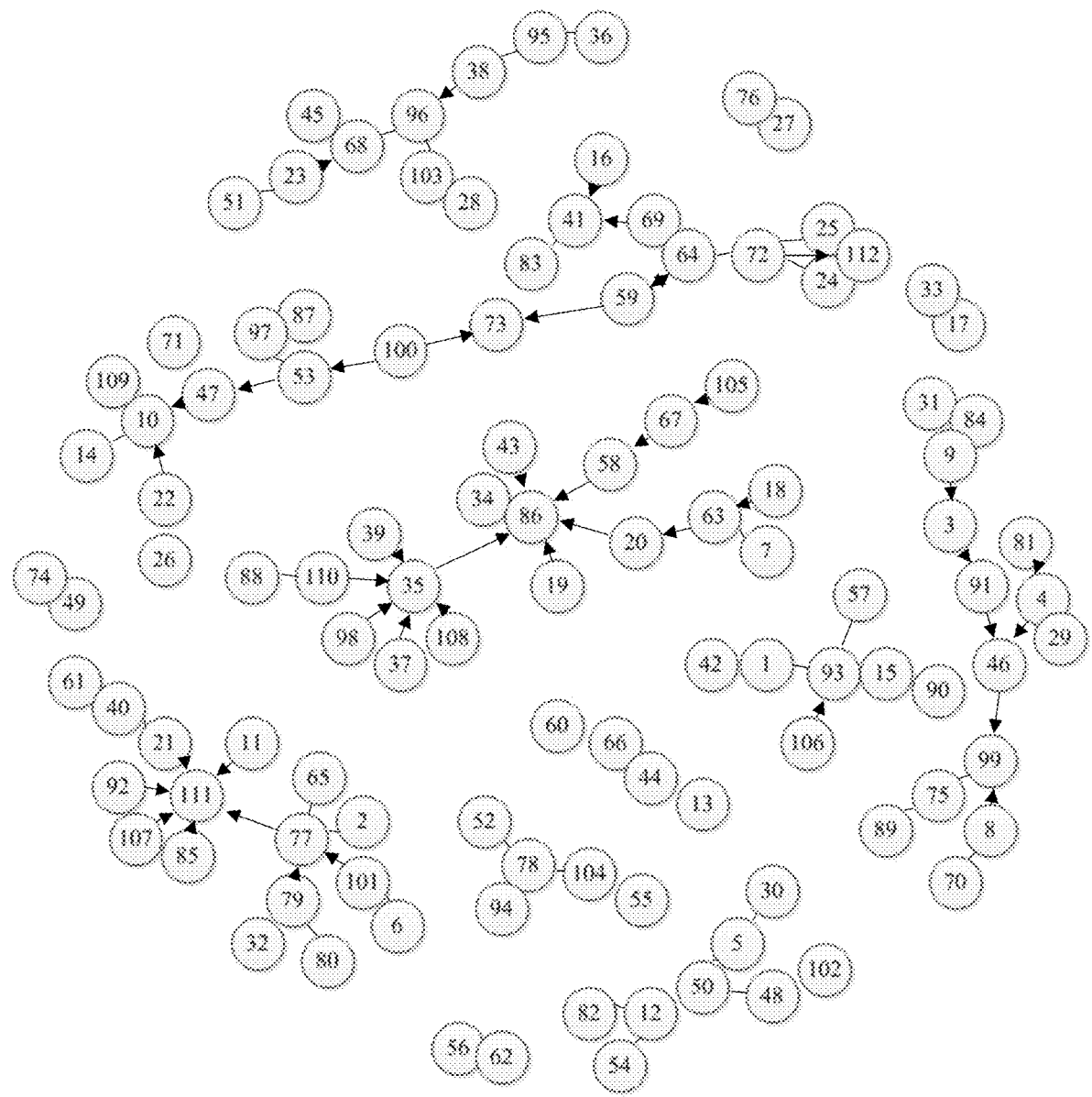
FIG. 7 is a visual depiction of a plurality of providers with problem list concepts combined into clusters and arranged to indicate similarity between providers.

Using the relationships shown in FIG. 7, it may be possible to determine which provider(s) is/are most similar to a given provider. Lines connecting one provider to another signify that the linked providers are most similar to one another. Arrows extending from one provider to another reflect directionality. For example, the arrow from provider "20" to provider "86" in the middle of the figure signifies that provider "86" is the closest match to provider "20" but that provider "20" is not necessarily the closest match to provider "86." Due to the nature of the data modeling, each provider may be sent to, at most, one other provider, although a single provider may be sent to by multiple providers.

Figure 8:
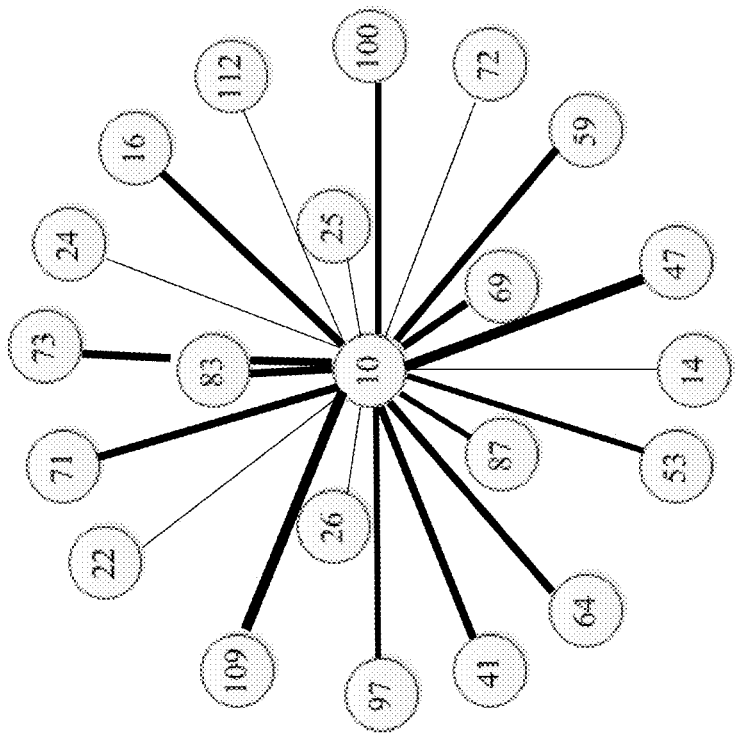
FIG. 8 is a visual depiction of a selected provider from among the providers of FIG. 4 and the providers most similar to the selected provider.

In another aspect, the system may receive a provider selection from a user and provide a different graphical representation of the other providers that the system has determined to be most similar based off the distance calculations and/or the clustering of providers. For example, FIG. 8 depicts one example of this representation, with the selected provider placed at the center of a provider mapping and the related providers displayed as radiating outward from that center. Related providers may be joined to the selected provider, e.g., via a line connecting provider IDs. Similarity may be represented by a thickness of the connecting line, with a thicker line signifying more closely-related providers. Additionally or alternatively, similarity also may be reflected by radial proximity of the other providers to the selected provider in the display.

Figure 9:
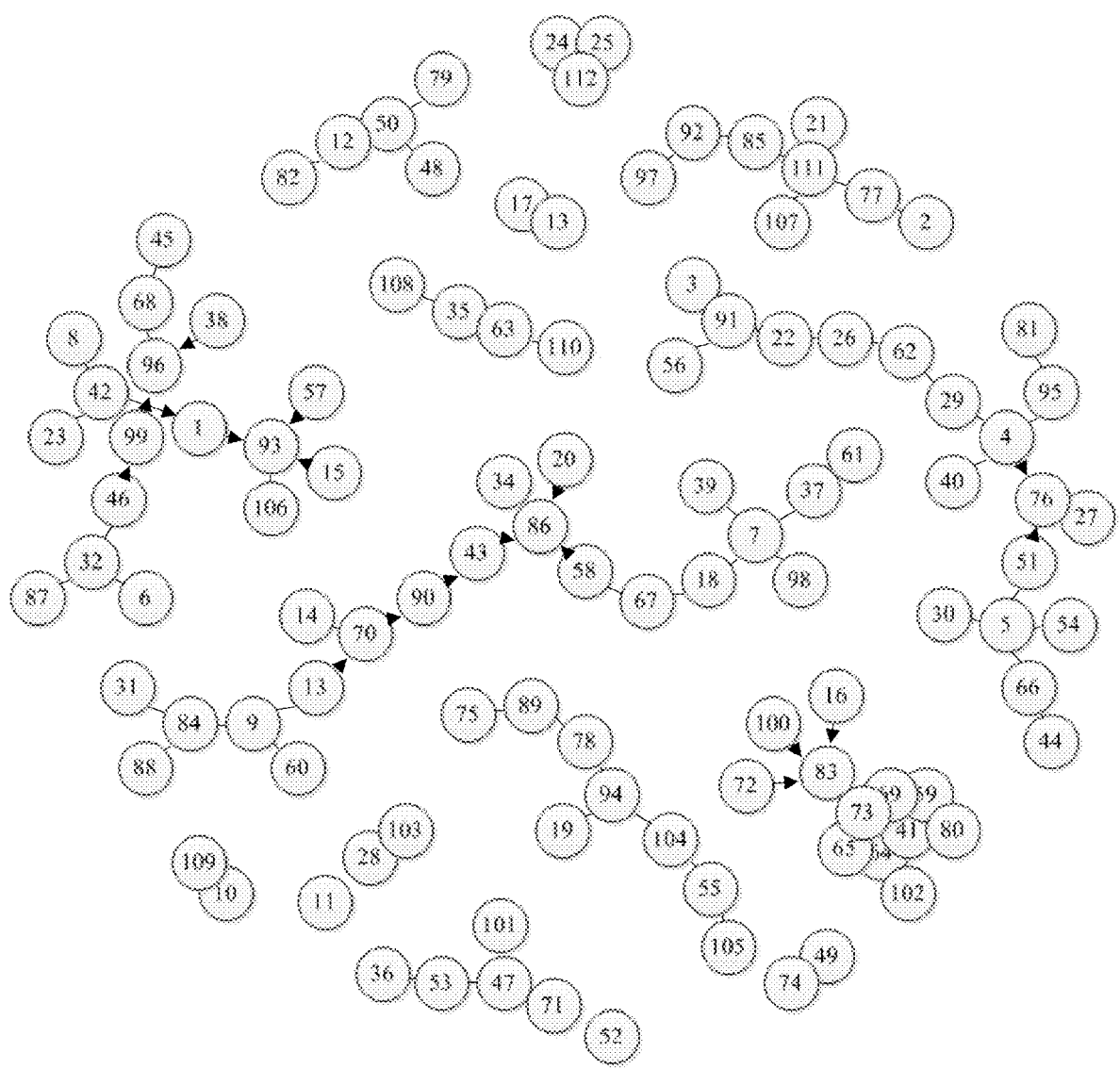
FIG. 9 is a visual depiction of a plurality of providers with problem list concepts combined into categories and arranged to indicate similarity between providers.

In another aspect, the system may be configured to use categories to calculate the distance matrix referred to above. Using these categories, the same general methodology set forth above may be followed, substituting clusters for categories. Since the list of problems in a category may not overlap completely with the list of problems in a cluster, the underlying problem counts may vary. As such, using categories instead of clusters may result in the same providers being mapped to different other providers, changing the display of logical relationships, as seen in FIG. 9.

Edges

The analysis may be refined further by applying a weight to the distance matrices based on cluster and category, generating a modified distance matrix according to the following formula:

$$d_{new} = W \times d_{category} + (1-w) \times d_{cluster},$$

where $w \in [0,1]$. The selection for the weight, $w$, may be user-defined in order to account for whether the weight should be more specific or more generic.

Figure 10:
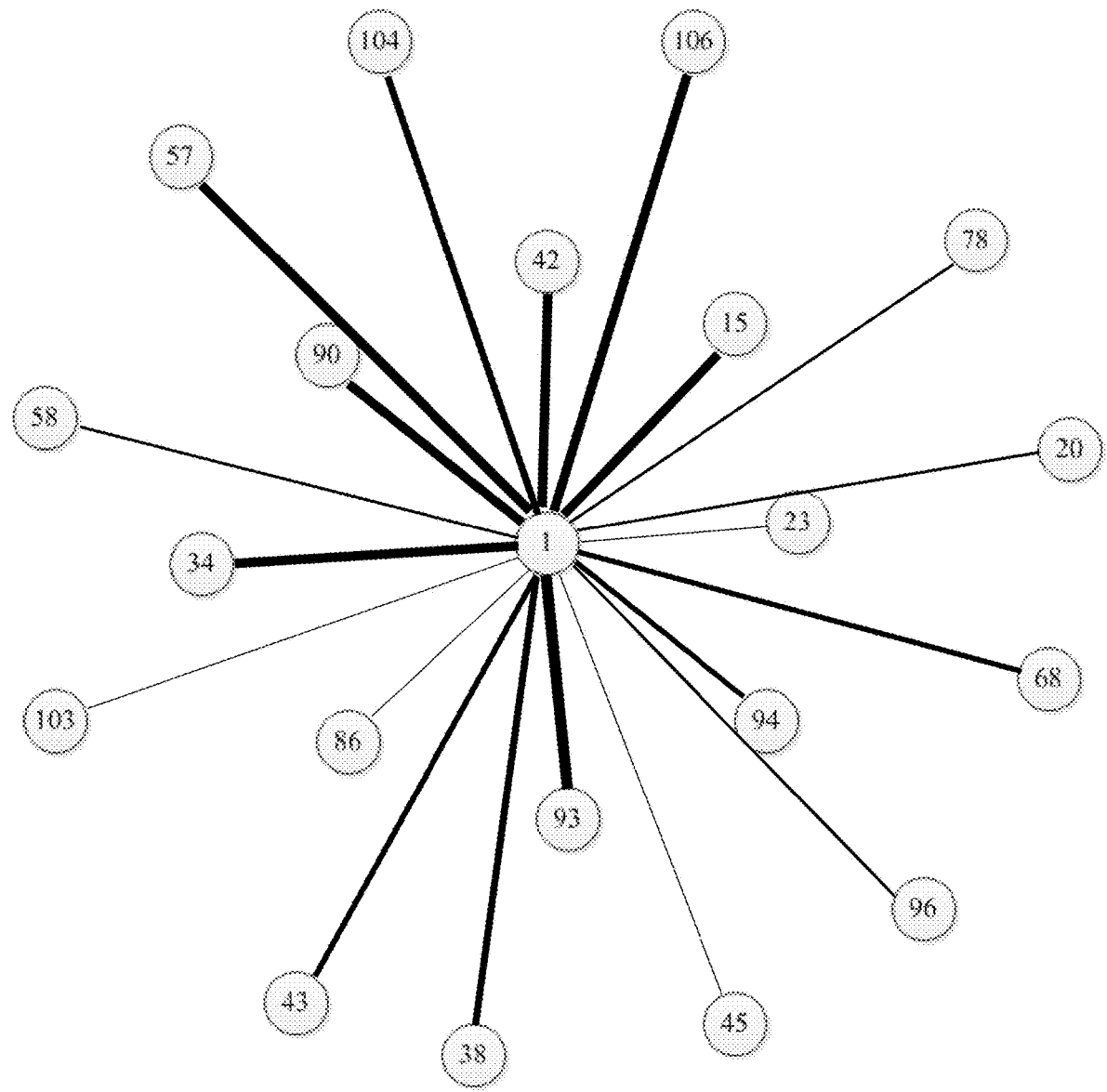
FIG. 10 is a visual depiction of a selected provider from among the providers of FIG. 6 and the providers most similar to the selected provider.

In order to provide more meaningful results to the user, the system may filter the results to a predetermined or user-selected number upon selection of a provider for which greater analysis is desired. For example, upon selection of provider number 1, FIG. 10 is one example of a graphical depiction of the twenty providers most similar to that selected provider, displayed as a similarity group surrounding that provider. It will be appreciated that the grouping may reflect more than just the providers provided as direct elements of a cluster as in FIGS. 4 and 6.

Figure 11:
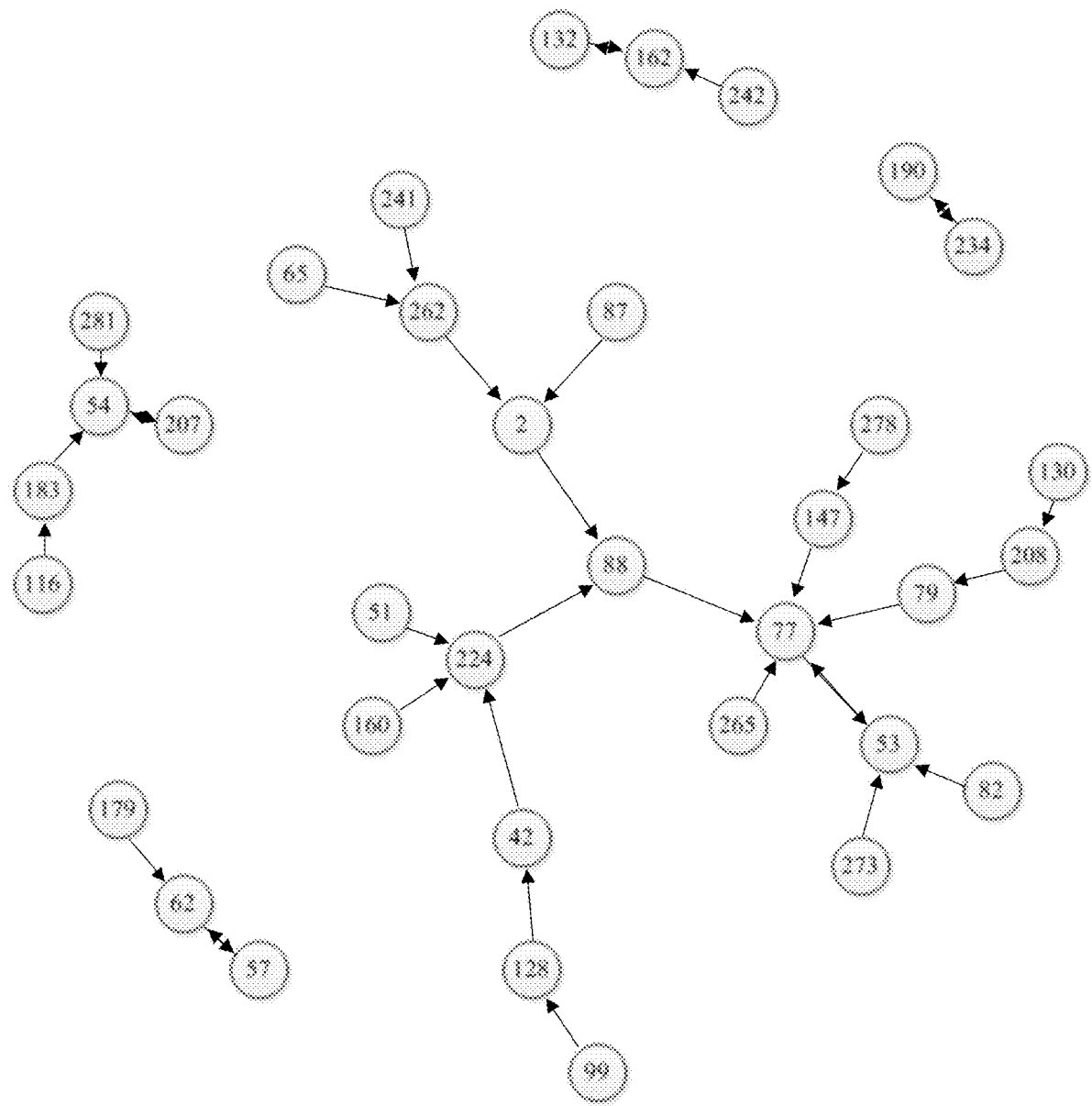
FIG. 11 is a visual depiction of a plurality of providers with problem list concepts recorded in a limited time span, combined into clusters, and arranged to indicate similarity between providers.

In still another aspect, the system may be configured to filter providers according to a temporal component of activity. For example, as seen in FIG. 11, only providers with relevant patient activity in the past predetermined or user-selected time period, e.g., the past month, may be used for comparative purposes. Alternatively, the system may accept user input of a different specific time period, e.g., the time span between 30 and 60 days ago. In either case, this filtering capacity may allow the user to search for providers with relevant activity either most recently or within the desired time period. In the former case, the filtering may be useful to filter out providers that have not had any relevant activity recently and, as such, may not be as useful. In the latter case, the filtering may be useful when a historical analysis is desired, such as determining a temporal or geographical origin or spread of particular disease.

Providers for which no relevant activity was recorded in the given time period may be hidden from presentation to the user. Alternatively, those other providers may be represented in the display, but they may be not connected to any other provider, reflecting their lack of commonality with the other providers.

Patient Analysis

Figure 12:
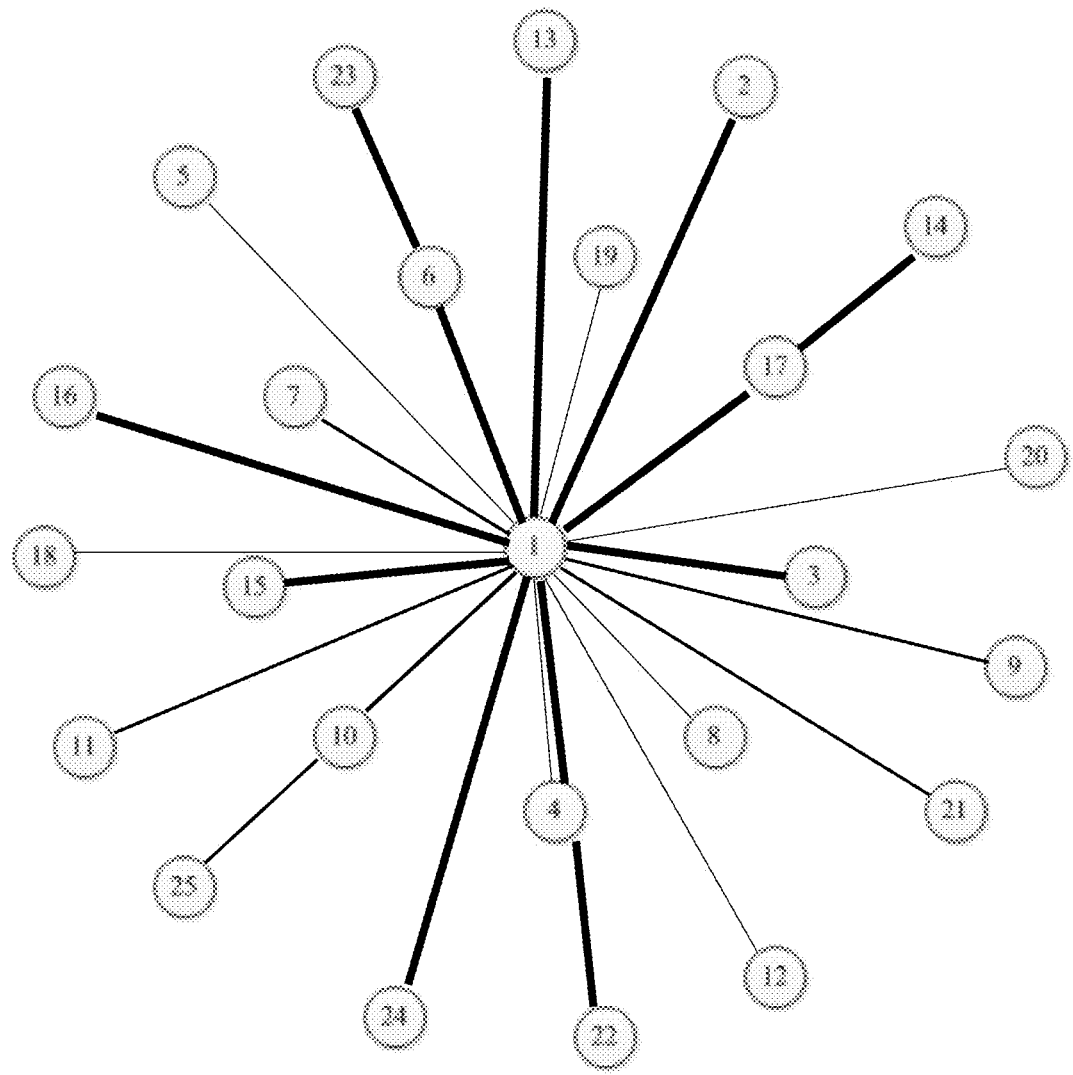
FIG. 12 is a visual depiction of a selected patient from among a plurality of patients with problem list concepts combined into clusters, the depiction arranged to indicate similarity between patients.

In addition to analyzing similarity on a provider basis, the system also may be configured to analyze patient similarity. Each patient may be assigned to one or more clusters, the clusters represented in a database table with one or more unique identifiers such as one or more cluster title entries. Patient similarity analysis using those cluster title variables may be accomplished in the same way as the provider analysis set forth above, and results may be displayed in a similar fashion as see, e.g., in FIG. 12.

Figure 13:
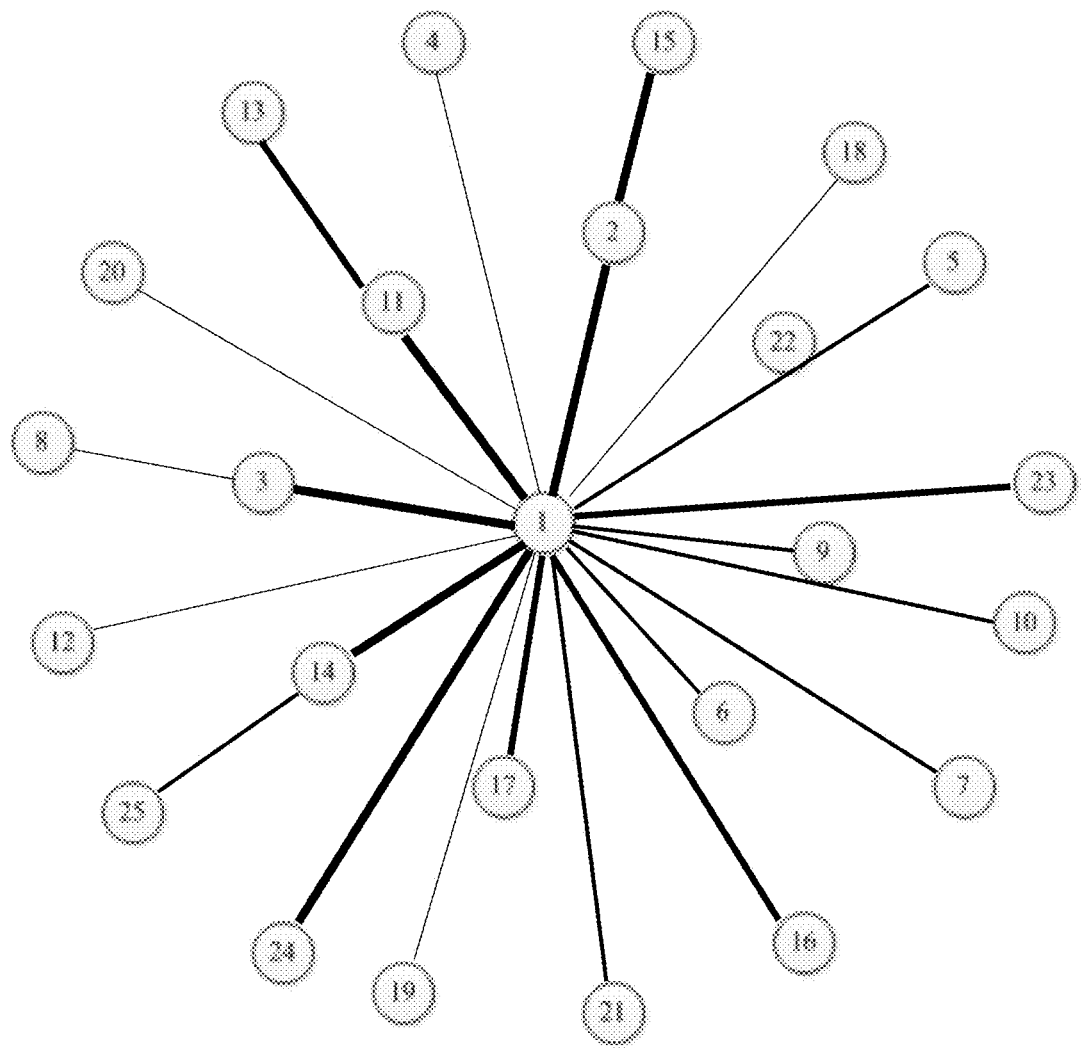
FIG. 13 is a visual depiction of a selected patient from among a plurality of patients with problem list concepts combined into categories, the depiction arranged to indicate similarity between patients.

Other patient analysis, using other patient-centric variables, may be carried out in the same way. Alternatively, as with the provider analysis described above, patient-centric analysis may be done using categories instead of clusters, with the results similarly changing, as depicted in FIG. 13.

Figure 14:
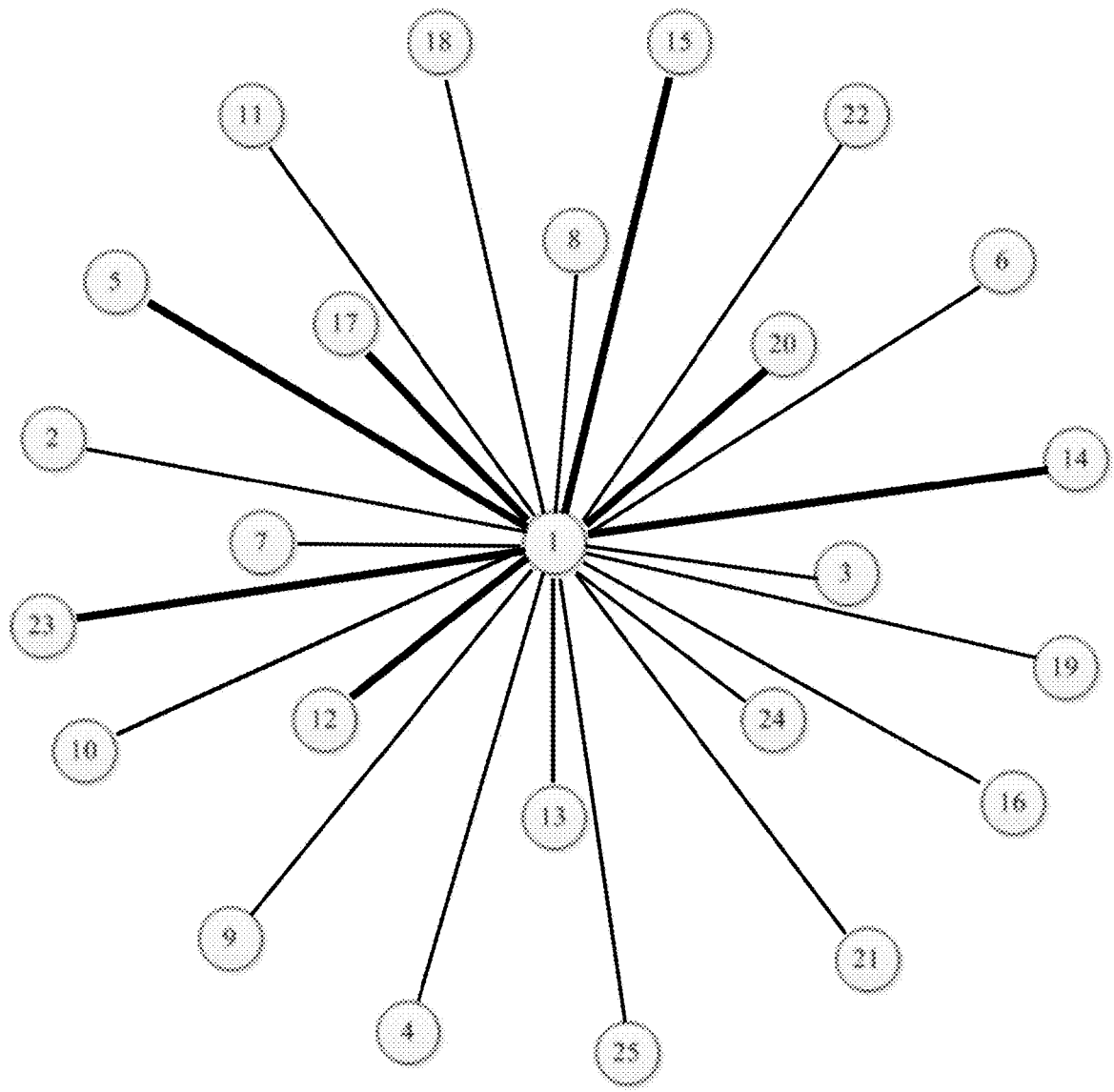
FIG. 14 is a visual depiction of a selected patient from among a plurality of patients analyzed for exact matches to problem list concepts, the depiction arranged to indicate similarity between patients.

In still another aspect, as seen in FIG. 14, patients may be ranked depending on whether they have the exact same problems, as opposed to just similar ones. As seen in that figure, the similarity scores may be identical for multiple other patients, reflecting the problem match.

Figure 15:
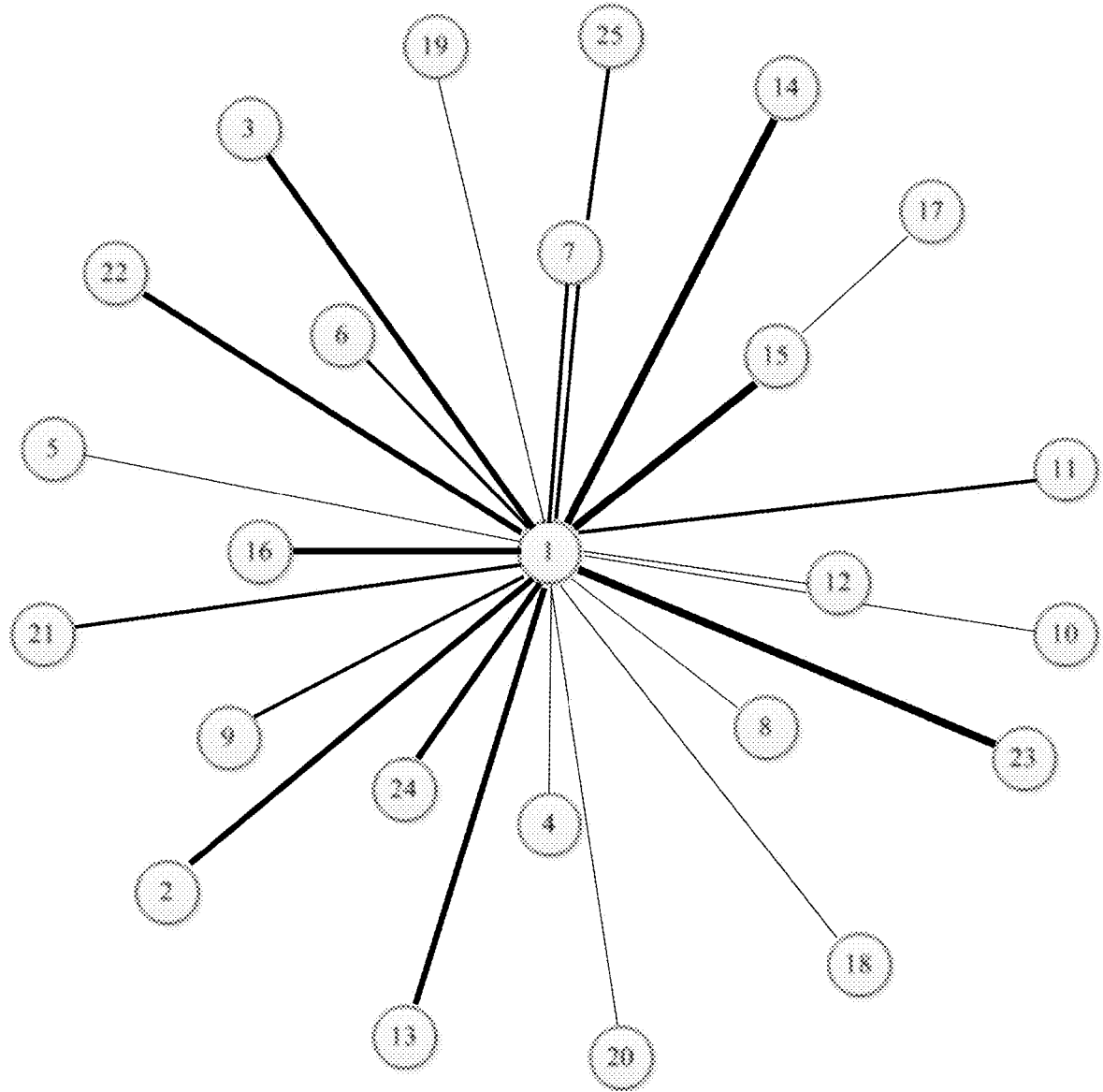
FIG. 15 is a visual depiction of a selected patient from among a plurality of patients analyzed, accounting equally for problem list concept matches and cluster similarity, the depiction arranged to indicate similarity between patients.
Figure 16:
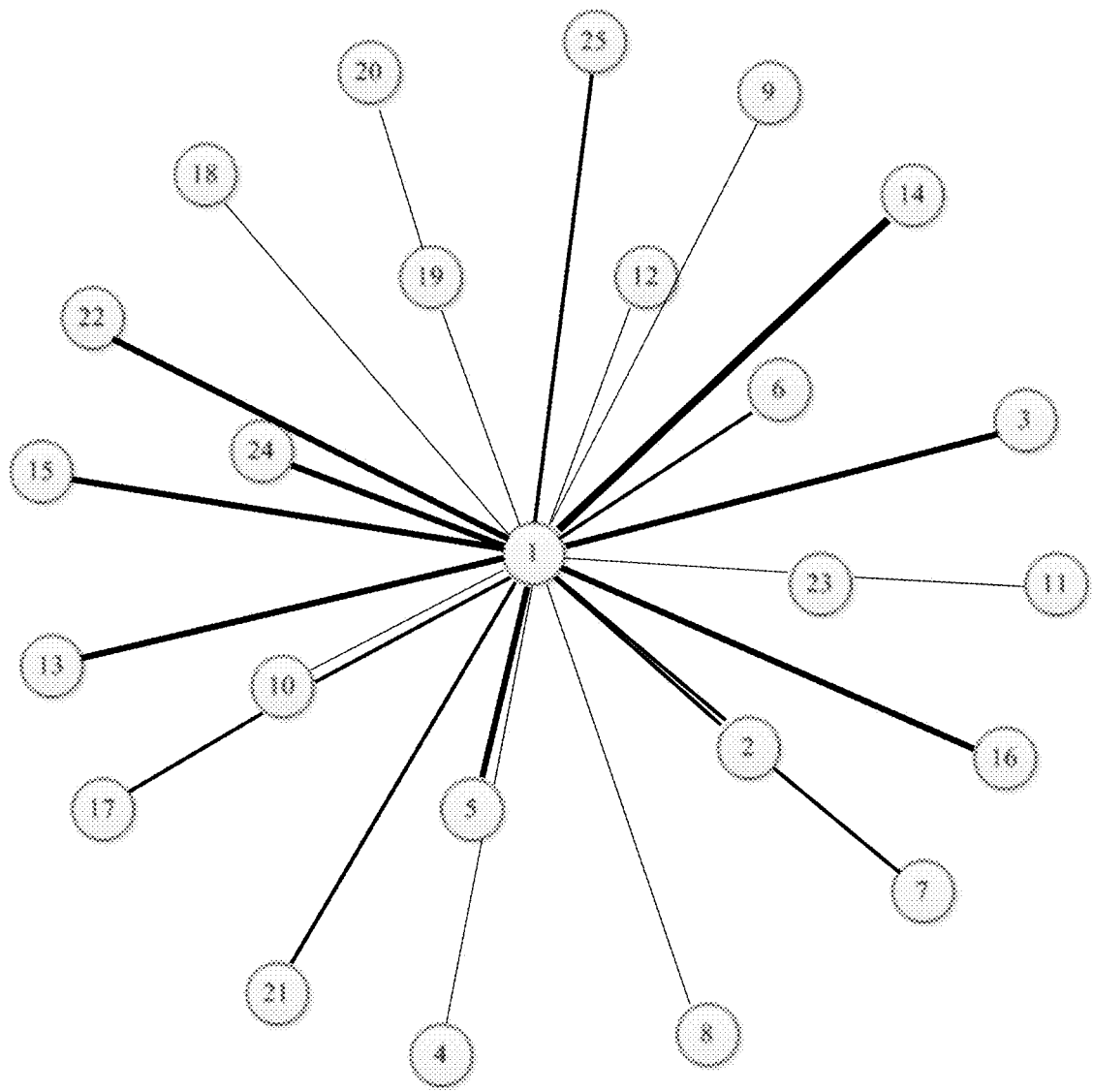
FIG. 16 is a visual depiction of a selected patient from among a plurality of patients analyzed, accounting more heavily for problem list concept matches as compared to cluster similarity, the depiction arranged to indicate similarity between patients.
Figure 17:
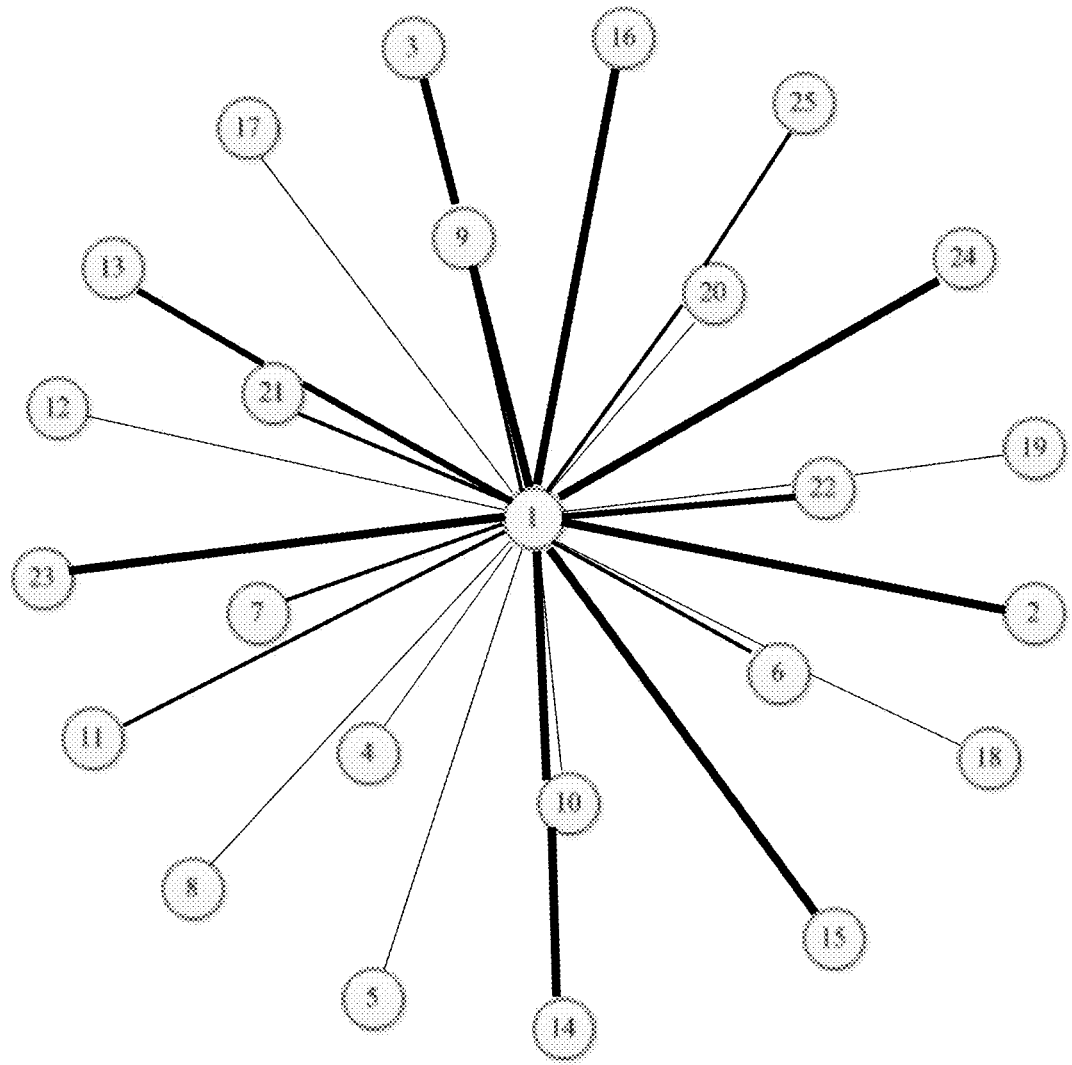
FIG. 17 is a visual depiction of a selected patient from among a plurality of patients analyzed, accounting more heavily for cluster similarity as compared to problem list concept matches, the depiction arranged to indicate similarity between patients.

Turning to FIG. 15, it further may be possible to analyze patients or providers based on a combination of problems and clusters. One or more problems and one or more clusters may be evaluated. Additionally, it may be possible to provider user weighting for one or more of the problems or clusters, e.g., if it is deemed that the presence of a particular problem or combination of problems is more significant than the other variables. In one aspect, any weight may be provided to each variable, provided that a sum of the weights is 1. For example, FIG. 15 reflects the use of a single problem and a single cluster variable, each weighted equally. Conversely, FIG. 16 reflects the use of the same problem and cluster variables, but with the problem weighted at 0.8 and the cluster weighted at 0.2. Still further, FIG. 17 reflects the use of the same problem and cluster variables, but with the problem weighted at 0.2 and the cluster weighted at 0.8.

In another aspect, any weights can be provided to each variable, and the system will normalize them in order to determine the relative weights as among each variable.

Additionally, it may be possible to refine the results by reducing the number of clusters being analyzed. For example, a data set may include 120 unique clusters as between 112 unique providers. Of those, 23 clusters may not include any relevant patient data, so that eliminating them from the analysis may yield 97 clusters.

Still further, the system may be configured to keep or eliminate clusters above or below a user-defined or predetermined correlation. For example, to avoid multicollinearity, or clusters that are highly correlated, the system may eliminate clusters with a maximum correlation above 0.7. In this example, this may reduce the number of clusters from 97 to 61, or essentially halving the number of clusters to be analyzed.

While it may seem counterintuitive to eliminate highly correlated clusters, the correlation may, in fact, represent an over-weighting of dependent information. For example, problems may be assigned to multiple clusters, e.g., a weight-related cluster and a diabetes cluster, where much of the information or many of the problems in one cluster also apply to the other cluster. In that case, similarity analysis using both clusters may, in effect, double-count those problems, skewing the impact the problems have on the distance analysis. Correlation determinations may be user-defined in one aspect and automatically determined, such as by comparing a number of overlapping problems in each cluster, a proportion of overlapping problems as compared to a total number of problems in each cluster, or via another algorithm, as would be appreciated by one of ordinary skill in the relevant art.

Outputs may include:

One or more indicators of similarity among providers based on clusters or categories, overall and/or within a specific set (e.g., a single account).

One or more indicators of similarity among the providers based on the combination of clusters and categories.

One or more indicators of similarity as above, partitioned over months or some other predefined or user-defined time segment.

A ranking of a predetermined or user-defined, e.g., top 20, providers similar to a specific provider based on the combination of clusters and categories.

A ranking of patients similar to a specific patient within a single provider based on clusters (category).

A ranking of patients similar to a specific patient within a single provider based on the exact problems, as reflected by encoding of those problems using interface terminology concepts or descriptions, and the clusters.

The system and method described herein may provider a user with one or more of the following benefits:

Identifying the single-most similar provider or a plurality of similar providers based on the problem lists associated with one or more of the providers' patients. This identification may be accomplished through a user interface that presents the relationships in a manner similar to FIGS. 7-17, where selection of a provider or patient may cause the display to be refreshed or updated with more specific information about that provider or patient, and/or with additional information explaining the basis for the similarity with that provider or patient and its upstream and/or downstream matches. The identification alternatively may be accomplished by providing a user interface that includes a list or table of either all providers or patients or, instead, of a predetermined or user-selected number of the closest matches. The list or table may be sortable, e.g., by closest match, and also may be selectable, such that additional information such as the basis for the similarity matches may be displayed upon user selection of a provider or patient. For patient matches, the user interface also may be configured such that, upon selection of a patient identifier, both the selected patient and the subject patient's problem lists may be displayed to facilitate comparison of the two.

Given a provider, the most similar providers can be determined and provided to the user as an ordered list, e.g., within an organization or a set of organizations, or over all users or providers for which the system has the necessary data.

An ability to rank providers based on counts or proportions or patients, with problems partitioned by one or more of clusters and categories.

Within a provider's data set, the same analysis can be performed on a patient-centric basis.

While the foregoing written description of the invention enables one of ordinary skill to make and use what is considered presently to be the best mode thereof, those of ordinary skill will understand and appreciate the existence of variations, combinations, and equivalents of the specific exemplary embodiment and method herein. The invention should therefore not be limited by the above described embodiment and method, but by all embodiments and methods within the scope and spirit of the invention as claimed.

We claim:

1. A method for extracting data from a plurality of electronic data repositories to provide provider and patient data similarity scoring, comprising:

encoding a plurality of electronic problem lists stored using one or more electronic health record ontologies on a networked computer system for a respective plurality of patients with concepts from a common electronic health record ontology, wherein the electronic problem lists are stored using the one or more electronic health record ontologies so as to be used with a respective electronic health record software package, wherein the plurality of electronic data repositories are maintained by a plurality of providers and wherein each of the patients is attributable to a respective provider;

parsing the concepts into a plurality of clusters or categories of concept groupings;

determining, for each of the providers and for all of the problems encoded to a respective concept within a cluster or category of concept groupings, a total number of patients that have at least one problem in the cluster or category of concept groupings, wherein a patient is associated with the cluster or category of concept groupings according to whether the patient has at least one problem in the cluster or category;

iterating the determining step for each of the remaining clusters or categories of concept groupings;

calculating, for each pair of providers, a distance between the providers using the results of the determining and iterating steps; and generating, on a display of a computer, a first user interface arranging at least a subset of the providers into one or more groups reflected by the plurality of clusters or categories, the first user interface providing, for each provider in the subset of providers, a visual representation of a closest match to that provider based on the distance between the providers, wherein the first user interface is selectable to generate, on the display, a second user interface in which a provider selected from the first user interface is depicted in conjunction with one or more of the other providers calculated to be closest to the selected provider, along with visual representations of a degree of closeness between those providers and the selected provider.

2. The method of claim 1, wherein the calculating step includes calculating a Minkowski distance of order 2 between each pair of providers.

3. The method of claim 1, wherein the calculating step includes normalizing the results of the determining and iterating steps by dividing those results by a respective provider's total number of patients.

4. The method of claim 1, wherein the common electronic health record ontology is an interface terminology.

5. The method of claim 4, wherein the problem list also is encoded, directly or indirectly, with a health record ontology selected from the group consisting of the Systematized Nomenclature of Medicine and the International Classification of Disease.

6. The method of claim 1, wherein the calculating step uses exact problem list matches as inputs.

7. The method of claim 6, wherein the results of the determining and iterating steps and the exact problem list matches are weighted equally.

8. The method of claim 6, wherein the results of the determining and iterating steps are weighted more heavily than the exact problem list matches.

9. The method of claim 6, where the exact problem list matches are weighted more heavily than the results of the determining and iterating steps.

10. The method of claim 1, wherein at least one of the electronic data repositories is an electronic health record repository.

11. The method of claim 1, wherein at least one of the electronic data repositories is a problem list log repository.

* * * * *